US012042656B2

(12) United States Patent
Doan et al.

(10) Patent No.: US 12,042,656 B2
(45) Date of Patent: Jul. 23, 2024

(54) BOLUS STIMULATION IN A NEUROSTIMULATION DEVICE PARTICULARLY USEFUL IN PROVIDING SUB-PERCEPTION STIMULATION

(71) Applicant: Boston Scientific Neuromodulation Corporation, Valencia, CA (US)

(72) Inventors: Que T. Doan, West Hills, CA (US); Michael A. Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 17/002,552

(22) Filed: Aug. 25, 2020

(65) Prior Publication Data

US 2020/0384270 A1    Dec. 10, 2020

Related U.S. Application Data

(63) Continuation-in-part of application No. PCT/US2020/040529, filed on Jul. 1, 2020, and a
(Continued)

(51) Int. Cl.
*A61N 1/36* (2006.01)

(52) U.S. Cl.
CPC ..... *A61N 1/36121* (2013.01); *A61N 1/36062* (2017.08); *A61N 1/36135* (2013.01);
(Continued)

(58) Field of Classification Search
CPC ............ A61N 1/36121; A61N 1/36062; A61N 1/36135; A61N 1/36175; A61N 1/36192;
(Continued)

(56) References Cited

U.S. PATENT DOCUMENTS

| 6,516,227 B1 | 2/2003 | Meadows et al. |
| 7,369,891 B2 * | 5/2008 | Augustijn ............. A61N 1/368 |
| | | 607/9 |

(Continued)

FOREIGN PATENT DOCUMENTS

| WO | PCT/US2020/036667 | 6/2020 |
| WO | PCT/US2020/040529 | 7/2020 |

OTHER PUBLICATIONS

International Search Report and Written Opinion regarding corresponding PCT Application No. PCT/US2020/047828, dated Dec. 15, 2020.
(Continued)

*Primary Examiner* — Joseph M Dietrich
*Assistant Examiner* — Ranjani Mari Sundaresan
(74) *Attorney, Agent, or Firm* — Lewis & Reese, PLLC

(57) ABSTRACT

A method and external device for providing sub-perception stimulation to a patient via an implantable stimulator device is disclosed. Stimulation parameters for the patient are determined that provide sub-perception stimulation to address a symptom of the patient. A schedule is determined to provide scheduled boluses of stimulation, where each bolus comprises a duration during which stimulation is applied to the patient in accordance with the stimulation parameters, and where the scheduled boluses are separated by off times when no stimulation is provided to the patient. Preferably, the duration of each of the scheduled boluses is 3 minutes or longer, and the duration of each of the off times is 30 minutes or greater. Additional boluses can be provided on demand in addition to the scheduled boluses by selecting an option on the external device, although the provision of such additional boluses may be constrained by a lockout period.

20 Claims, 12 Drawing Sheets

Related U.S. Application Data continuation-in-part of application No. 16/741,258, filed on Jan. 13, 2020, now abandoned, and a continuation-in-part of application No. 16/738,786, filed on Jan. 9, 2020, which is a continuation-in-part of application No. 16/657,560, filed on Oct. 18, 2019, which is a continuation-in-part of application No. 16/460,640, filed on Jul. 2, 2019, and a continuation-in-part of application No. 16/460,655, filed on Jul. 2, 2019, now Pat. No. 11,338,127, and a continuation-in-part of application No. 16/100,904, filed on Aug. 10, 2018, now Pat. No. 10,576,282.

(60) Provisional application No. 62/986,365, filed on Mar. 6, 2020, provisional application No. 62/916,958, filed on Oct. 18, 2019, provisional application No. 62/803,330, filed on Feb. 8, 2019, provisional application No. 62/693,543, filed on Jul. 3, 2018, provisional application No. 62/544,656, filed on Aug. 11, 2017.

(52) U.S. Cl.
CPC ..... *A61N 1/36175* (2013.01); *A61N 1/36192* (2013.01); *A61N 1/36196* (2013.01)

(58) Field of Classification Search
CPC ............ A61N 1/36196; A61N 1/36071; A61N 1/36164; A61N 1/36132; A61N 1/36167; A61N 1/37247
See application file for complete search history.

(56) References Cited

U.S. PATENT DOCUMENTS

| | | | |
|---|---|---|---|
| 8,568,356 | B2 | 10/2013 | Lebel et al. |
| 8,606,362 | B2 | 12/2013 | He et al. |
| 8,620,436 | B2 * | 12/2013 | Parramon et al. |
| 9,327,123 | B2 * | 5/2016 | Yamasaki ................ A61B 5/24 |
| 10,576,282 | B2 | 3/2020 | Doan et al. |
| 2010/0010566 | A1 * | 1/2010 | Thacker ............. A61N 1/37247 607/46 |
| 2011/0106214 | A1 | 5/2011 | Carbunaru et al. |
| 2012/0130448 | A1 * | 5/2012 | Woods ............... A61N 1/36185 607/46 |
| 2013/0282078 | A1 | 10/2013 | Wacnik |
| 2014/0364919 | A1 | 12/2014 | Doan |
| 2014/0364920 | A1 * | 12/2014 | Doan ................. A61N 1/37247 607/46 |
| 2015/0231402 | A1 | 8/2015 | Aghassian |
| 2015/0360038 | A1 | 12/2015 | Zottola et al. |
| 2016/0144183 | A1 | 5/2016 | Marnfeldt |
| 2017/0050033 | A1 * | 2/2017 | Wechter ............. A61N 1/37247 |
| 2017/0189688 | A1 * | 7/2017 | Steinke ................. G16H 40/63 |
| 2018/0071513 | A1 | 3/2018 | Weiss et al. |
| 2018/0093093 | A1 | 4/2018 | Courtine et al. |
| 2019/0009094 | A1 | 1/2019 | Zhang et al. |
| 2019/0046800 | A1 | 2/2019 | Doan et al. |
| 2020/0147400 | A1 | 5/2020 | Moffitt et al. |

OTHER PUBLICATIONS

Abbott Laboratories, "BOLD: BurstDR™ micrOdosing stimuLation in De-novo patients," Clinical Investigation Plan, published at https://clinicaltlials.gov/ProvidedDocs/56/NCT03350256/Prot_SAP_000.pdf (May 19, 2017).
U.S. Appl. No. 62/544,656, Gu et al.
U.S. Appl. No. 62/986,365, Huertas Fernandez et al.
Communication Pursuant to Article 94(3) EPC regarding corresponding European Patent Application Serial No. 1 20765458.3, dated Apr. 12, 2023.

* cited by examiner

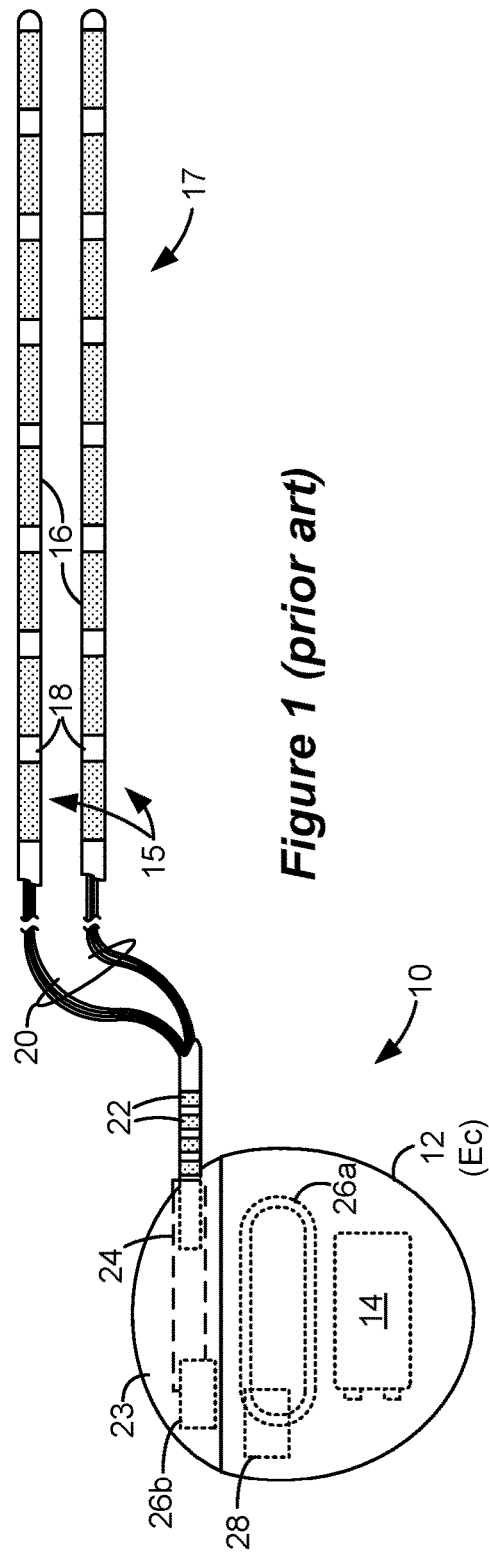
*Figure 1 (prior art)*
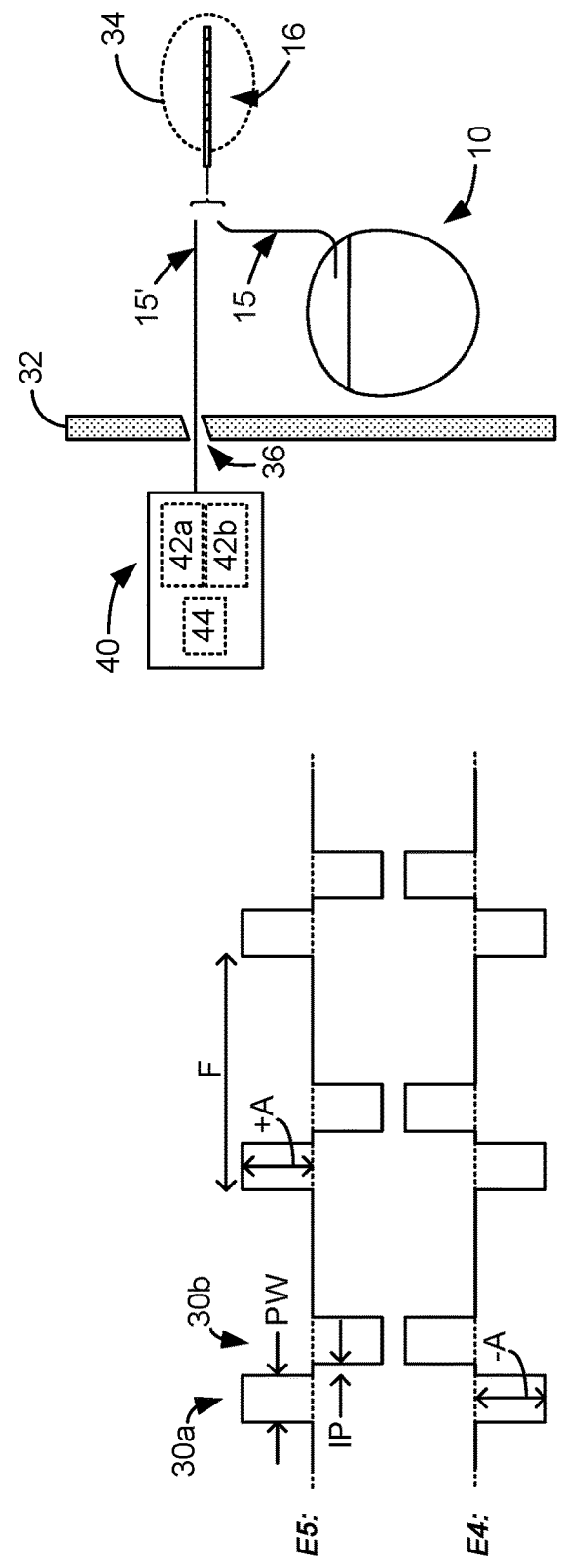
*Figure 3 (prior art)*
*Figure 2 (prior art)*

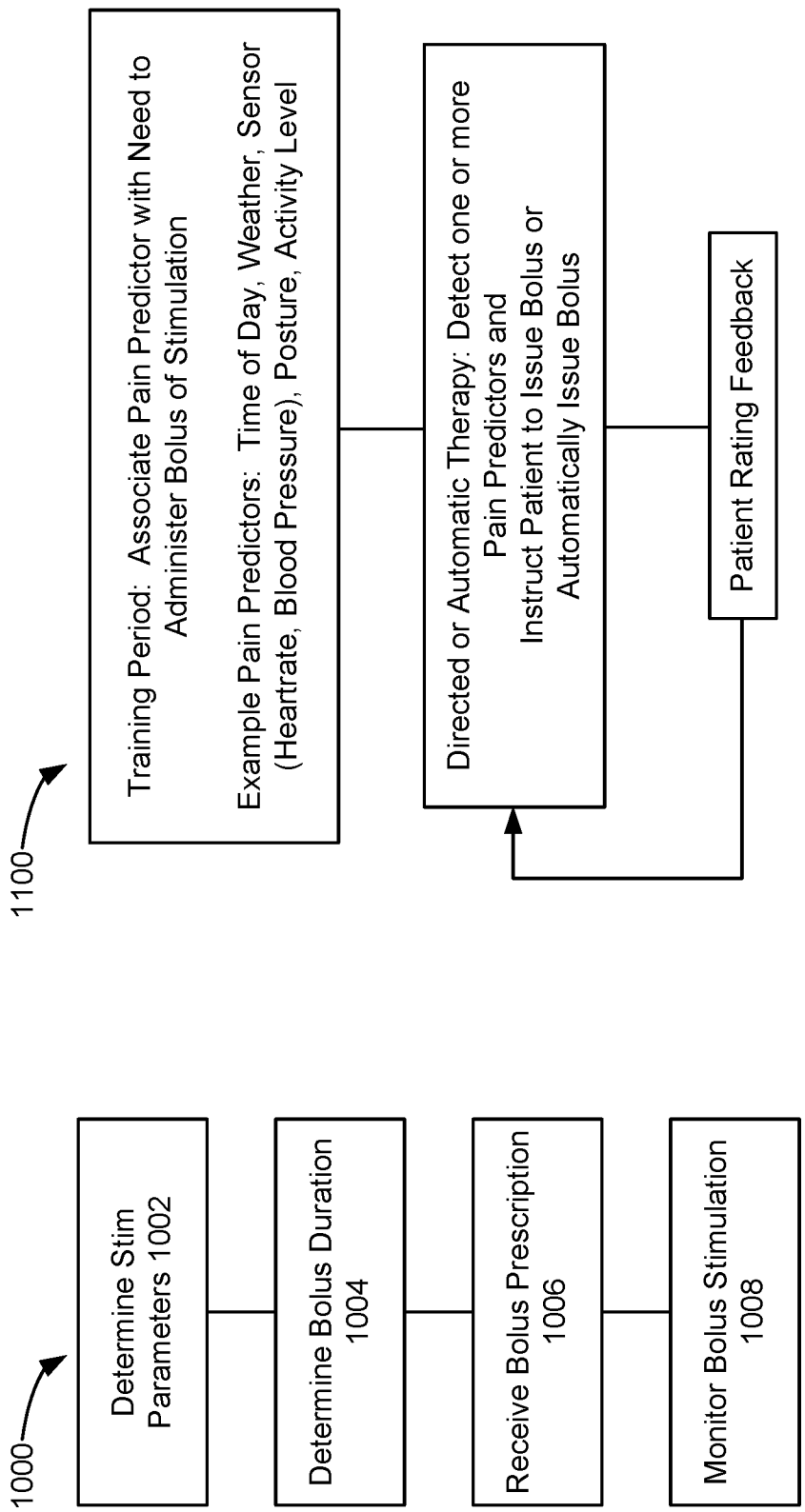

| | SP2 continuous (no bolus) | SP3 continuous (no bolus) | SP1 continuous (no bolus) | SP2 with bolus (t2 = 30 min, t3 = 90 min) | SP2 with bolus (t2 = 30 min, t3 = 240 min) | SP3 with bolus (t2 = 30 min, t3 = 90 min) | SP3 with bolus (t2 = 30 min, t3 = 240 min) |
|---|---|---|---|---|---|---|---|
| Medium neural dose | Rating = 4 | Rating = 5 | Rating = 3 | Rating = 3 | Rating = 4 | *Rating = 5* | Rating = 3 |
| High neural dose | Rating = 4 | *Rating = 5* | Rating = 3 | Rating = 3 | Rating = 3 | Rating = 4 | Rating = 4 |
| Low neural dose | Rating = 4 | Rating = 4 | Rating = 3 | *Rating = 5* | Rating = 4 | Rating = 3 | Rating = 3 |

*Figure 16B*

BOLUS STIMULATION IN A NEUROSTIMULATION DEVICE PARTICULARLY USEFUL IN PROVIDING SUB-PERCEPTION STIMULATION

CROSS REFERENCE TO RELATED APPLICATIONS

This application is continuation-in-part of U.S. patent application Ser. No. 16/741,258, filed Jan. 13, 2020, which is a non-provisional of U.S. Provisional Patent Application Ser. No. 62/916,958, filed Oct. 18, 2019.

This application is also a continuation-in-part of U.S. patent application Ser. No. 16/738,786, filed Jan. 9, 2020, which is a continuation-in-part of U.S. patent application Ser. No. 16/657,560, filed Oct. 18, 2019, which is a continuation-in-part of:

- U.S. patent application Ser. No. 16/100,904, filed Aug. 10, 2018 (now U.S. Pat. No. 10,576,282), which is a non-provisional application of U.S. Provisional Patent Application Ser. Nos. 62/693,543, filed Jul. 3, 2018, and 62/544,656, filed Aug. 11, 2017;
- U.S. patent application Ser. No. 16/460,640, filed Jul. 2, 2019, which is a non-provisional application of U.S. Provisional Patent Application Ser. No. 62/803,330, filed Feb. 8, 2019; and
- U.S. patent application Ser. No. 16/460,655, filed Jul. 2, 2019, which is a non-provisional application of U.S. Provisional Patent Application Ser. No. 62/803,330, filed Feb. 8, 2019.

This application is also a continuation-in-part of Patent Cooperation Treaty (PCT) Application Serial No. PCT/US2020/040529, filed Jul. 1, 2020, which is a non-provisional of U.S. Provisional Patent Application Ser. No. 62/986,365, filed Mar. 6, 2020.

Priority is claimed to these above-referenced applications, and all are incorporated by reference in their entireties.

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

In the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal electrodes 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

In the example of FIG. 2, electrode E5 has been selected as an anode, and thus provides pulses which source a positive current of amplitude +A to the tissue. Electrode E4 has been selected as a cathode, and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripole stimulation, quadripole stimulation, etc.).

The pulses as shown in FIG. 2 are biphasic, comprising a first phase 30a, followed quickly thereafter by a second phase 30b of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30a and discharged (be recovered) during the second phase 30b. In the example shown, the first and second phases 30a and 30b have the same duration and amplitude (although opposite polarities), which ensures the same amount of charge during both phases. However, the second phase 30b may also be charged balance with the first phase 30a if the integral of the amplitude and durations of the two phases are equal in magnitude, as is well known. The width of each pulse, PW, is defined here as the duration of first pulse phase 30a, although pulse width could also refer to the total duration of the first and second pulse phases 30a and 30b as well. Note that an interphase period (IP) during which no stimulation is provided may be provided between the two phases 30a and 30b.

IPG 10 includes stimulation circuitry 28 that can be programmed to produce the stimulation pulses at the electrodes as defined by the stimulation program. Thus, the IPG 10 acts as a power supply to deliver power to the electrodes for providing stimulation to the patient. Stimulation circuitry 28 can for example comprise the circuitry described in U.S. Patent Application Publications 2018/0071513 and 2018/0071520, or described in U.S. Pat. Nos. 8,606,362 and 8,620,436. These references are incorporated herein by reference.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer 50. Both of devices 45 and 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

The external controller 45 can also have control circuitry 48 which can include a microprocessor, microcomputer, an FPGA, other digital logic structures, an Applicant Specific Integrated Circuit (ASIC), etc., which is capable of executing instructions an electronic device. Control circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

If the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 5. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A. Likewise, electrode E4 has been selected as the only cathode to sink current, and this electrode receives X=100% of that cathodic current, −A.

The GUI 64 as shown specifies only a pulse width PW of the first pulse phase 30a. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30a and 30b (e.g., each having a duration of PW, and with opposite polarities +A and −A). An advanced menu 88 can also be used (among other things) to define the relative durations and amplitudes of the pulse phases 30a and 30b, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion.

While GUI 64 is shown as operating in the clinician programmer 50, the user interface of the external controller 45 may provide similar functionality.

FIG. 6 shows an alternative embodiment of an implantable SCS system 600 comprising an implanted electrode lead 602 having electrodes 16 disposed thereon. The SCS system 600 does not use an implanted IPG to provide power for electrical stimulation. Instead, power is provided via radio frequency (RF) transmission through the patient's tissue 32 from an external power supply (EPS) 604. The EPS has an RF antenna 606 configured to transmit RF power and the implanted lead 602 comprises an antenna 608 configured to receive the RF power. The implanted lead 602 also has simple circuitry (not shown) configured to rectify the RF power and generate pulses. As with the IPG system described above, the RF-powered system 600 may use an external controller 45 to control and transmit stimulation parameters. However, in the system 600, the external controller 45 provides stimulation parameters to the EPS 604, rather than to an implanted IPG. While the EPS 604 and the external controller 45 are illustrated as separate units in FIG. 6, the EPS 604 and the external controller 45 may be combined as a single unit. The illustrated SCS system 600 has an advantage over the system illustrated in FIG. 1 in that the system 600 does not require a surgical procedure to implant an IPG (10, FIG. 1) and tunnel lead wires (20, FIG. 1) between the IPG and the electrode leads. However, a disadvantage of the system 600 (FIG. 6) is that the patient must position the EPS 604 near their tissue any time that they wish to receive stimulation. The EPS 604 may be carried in a belt, pouch or other carrying device, for example. Systems as shown in FIG. 6, which rely on RF energy provided by an EPS are referred to herein as "RF systems."

SUMMARY

An external device is disclosed configured to communicate with an implantable stimulator device implanted in a patient, comprising: control circuitry configured to: provide stimulation parameters for the patient to address a symptom of the patient, provide a schedule for the provision of scheduled boluses of stimulation for the patient, wherein each scheduled bolus comprises a first duration during which stimulation is applied to the patient in accordance with the stimulation parameters, wherein the scheduled boluses are separated by off times when no stimulation is provided to the patient, wherein the first duration of each of the scheduled boluses is 3 minutes or longer, and wherein a second duration of each of the off times is 30 minutes or greater, and transmit instructions to cause the implantable stimulator device to provide the scheduled boluses to neural tissue of the patient according to the schedule.

In one example, the stimulation parameters provide sub-perception stimulation to address a symptom of the patient. In one example, the implantable stimulator device comprises a spinal cord stimulator. In one example, the stimulation provided during each scheduled bolus comprises a sequence of periodic pulses. In one example, the stimulation parameters comprise one or more of an amplitude of the pulses, a pulse width of the pulses, or a frequency of the pulses. In one example, the frequency is 10 kHz or less. In one example, the frequency is 1 kHz or less. In one example, the amplitude comprises a constant current amplitude. In one example, the first durations of the scheduled boluses vary. In one example, the second durations of the off times vary. In one example, the control circuitry is further configured to determine an activity of the patient or to receive information indicative of an activity of the patient. In one example, the control circuitry is further configured to adjust either or both of the first durations of the scheduled boluses or the second durations of off times in accordance with the determined activity or the information indicative of the activity. In one example, the stimulation parameters are determined in accordance with the determined activity or the information indicative of the activity. In one example, the external device comprises a graphical user interface. In one example, the control circuitry is further configured to receive at a first time an input at the graphical user interface to immediately provide an additional bolus of stimulation. In one example, the control circuitry is further configured to transmit instructions to cause the implantable stimulator device to immediately provide the additional bolus of stimulation to the neural tissue of the patient in addition to providing the scheduled boluses. In one example, the control circuitry is programmed with a lockout period, wherein the control circuitry is further configured to transmit instructions to cause the implantable stimulator device to immediately provide the additional bolus of stimulation to the neural tissue only if a third duration between the first time and a preceding one of the scheduled boluses is equal to or longer than the lockout period. In one example, the control circuitry is further configured to reschedule at least one of the scheduled boluses after the additional bolus in accordance with the lockout period.

A method is disclosed for providing stimulation to a patient using an implantable stimulator device, comprising: determining stimulation parameters for the patient to address a symptom of the patient; determining a schedule for the provision of scheduled boluses of stimulation for the patient, wherein each bolus comprises a first duration during which stimulation is applied to the patient in accordance with the stimulation parameters, wherein the scheduled boluses are separated by off times when no stimulation is provided to the patient, wherein the first duration of each of the scheduled boluses is 3 minutes or longer, and wherein a second duration of each of the off times is 30 minutes or greater; and providing, using the implantable stimulator device, the scheduled boluses to neural tissue of the patient according to the schedule.

In one example, the stimulation parameters provide sub-perception stimulation to address a symptom of the patient. In one example, the neural tissue comprises a spinal cord of the patient. In one example, the stimulation provided during each scheduled bolus comprises a sequence of periodic pulses. In one example, the stimulation parameters comprise one or more of an amplitude of the pulses, a pulse width of the pulses, or a frequency of the pulses. In one example, the frequency is 10 kHz or less. In one example, the frequency is 1 kHz or less. In one example, the amplitude comprises a constant current amplitude. In one example, the first durations of the scheduled boluses vary. In one example, the second durations of the off times vary. In one example, the method further comprises determining an activity of the patient. In one example, either or both of the first durations of the scheduled boluses or the second durations of off times are adjusted in accordance with the determined activity. In one example, the stimulation parameters are determined in accordance with the determined activity. In one example, the activity of the patient is determined using an activity sensor. In one example, the activity sensor is within the implantable stimulator device. In one example, the stimulation parameters are determined in an external device in communication with the implantable stimulator device, and wherein the schedule is determined in the external device. In one example, information concerning the boluses is transmitted to the implantable stimulator device from an external device in communication with the implantable stimulator device, wherein the external device comprises a graphical user interface. In one example, the method further comprises receiving from the patient at a first time an input at the graphical user interface to immediately provide an additional bolus of stimulation. In one example, the method further comprises immediately providing the additional bolus to the neural tissue in addition to providing the scheduled boluses. In one example, the graphical user interface is programmed with a lockout period, further comprising immediately providing the additional bolus of stimulation to the neural tissue only if a third duration between the first time and a preceding one of the scheduled boluses is equal to or longer than the lockout period. In one example, the method further comprises rescheduling at least one of the scheduled boluses after the additional bolus in accordance with the lockout period.

An external device is disclosed configured to communicate with an implantable stimulator device implanted in a patient, comprising: control circuitry configured to: provide stimulation parameters for the patient to address a symptom of the patient, provide a schedule for the provision of scheduled boluses of stimulation for the patient, wherein each scheduled bolus comprises a first duration during which stimulation is applied to the patient in accordance with the stimulation parameters, wherein the scheduled boluses are separated by off times of a second duration when no stimulation is provided to the patient, receive at a first time an input at a graphical user interface of the external device to immediately provide an additional bolus of stimulation, and transmit instructions to cause the implantable stimulator device to provide at least the scheduled boluses to neural tissue of the patient according to the schedule.

In one example, the stimulation parameters provide sub-perception stimulation to address a symptom of the patient. In one example, the implantable stimulator device comprises a spinal cord stimulator. In one example, the first duration of each of the scheduled boluses is 3 minutes or longer, and wherein the second duration of each of the off times is 30 minutes or greater. In one example, the stimulation provided during each scheduled bolus comprises a sequence of periodic pulses. In one example, the stimulation parameters comprise one or more of an amplitude of the pulses, a pulse width of the pulses, or a frequency of the pulses. In one example, the frequency is 10 kHz or less. In one example, the frequency is 1 kHz or less. In one example, the amplitude comprises a constant current amplitude. In one example, the first durations of the scheduled boluses vary. In one example, the second durations of the off times vary. In one example, the control circuitry is further configured to determine an activity of the patient or to receive information indicative of an activity of the patient. In one example, the control circuitry is further configured to adjust either or both of the first durations of the scheduled boluses or the second durations off times in accordance with the determined activity or the information indicative of the activity. In one example, the stimulation parameters are determined in accordance with the determined activity or the information indicative of the activity. In one example, the control circuitry is configured to transmit instructions to cause the implantable stimulator device to immediately provide the additional bolus of stimulation to the neural tissue of the patient in addition to providing the scheduled boluses. In one example, the control circuitry is programmed with a lockout period, wherein the control circuitry is configured to transmit instructions to cause the implantable stimulator device to immediately provide the additional bolus of stimulation to the neural tissue only if a third duration between the first time and a preceding one of the scheduled boluses is equal to or longer than the lockout period. In one example, the control circuitry is further configured to reschedule at least one of the scheduled boluses after the additional bolus in accordance with the lockout period.

A method is disclosed for providing stimulation to a patient using an implantable stimulator device and an external device in communication with the implantable stimulator device, comprising: determining stimulation parameters for the patient to address a symptom of the patient; determining a schedule for the provision of scheduled boluses of stimulation for the patient, wherein each scheduled bolus comprises a first duration during which stimulation is applied to the patient in accordance with the stimulation parameters, wherein the scheduled boluses are separated by off times of a second duration when no stimulation is provided to the patient; receiving from the patient at a first time an input at a graphical user interface of the external device to immediately provide an additional bolus of stimulation; and providing, using the implantable stimulator device, at least the scheduled boluses to neural tissue of the patient according to the schedule.

In one example, the stimulation parameters provide sub-perception stimulation to address a symptom of the patient. In one example, the neural tissue comprises a spinal cord of the patient. In one example, the first duration of each of the scheduled boluses is 3 minutes or longer, and wherein the second duration of each of the off times is 30 minutes or greater. In one example, the stimulation provided during each scheduled bolus comprises a sequence of periodic pulses. In one example, the stimulation parameters comprise one or more of an amplitude of the pulses, a pulse width of the pulses, or a frequency of the pulses. In one example, the frequency is 10 kHz or less. In one example, the frequency is 1 kHz or less. In one example, the amplitude comprises a constant current amplitude. In one example, the first durations of the scheduled boluses vary. In one example, the second durations of the off times vary. In one example, the method further comprises determining an activity of the patient. In one example, either or both of the first durations of the scheduled boluses or the second durations of the off times are adjusted in accordance with the determined activity. In one example, the stimulation parameters are determined in accordance with the determined activity. In one example, the activity of the patient is determined using an activity sensor. In one example, the activity sensor is within the implantable stimulator device. In one example, the stimulation parameters are determined at the external device, and wherein the schedule is determined at the external device. In one example, the method further comprises immediately providing the additional bolus to the neural tissue in addition to providing the scheduled boluses. In one example, the graphical user interface is programmed with a lockout period, further comprising immediately providing the additional bolus of stimulation to the neural tissue only if a third duration between the first time and a preceding one of the scheduled boluses is equal to or longer than the lockout period. In one example, the method further comprises rescheduling at least one of the scheduled boluses after the additional bolus in accordance with the lockout period.

An external device is disclosed configured to communicate with an implantable stimulator device implanted in a patient, comprising: control circuitry configured to: provide stimulation parameters for the patient, wherein the stimulation parameters provide sub-perception stimulation pulses to address a symptom of the patient, receive a first input to program a first duration, receive at a first time a second input at a graphical user interface of the external device to immediately provide a single bolus of stimulation, and transmit instructions to cause the implantable stimulator device to provide the single bolus to neural tissue of the patient for the first duration, wherein the single bolus comprises a plurality of periodic sub-perception stimulation pulses formed in accordance with the stimulation parameters.

In one example, the implantable stimulator device comprises a spinal cord stimulator. In one example, the first duration of the single bolus is 3 minutes or longer. In one example, the stimulation parameters comprise one or more of an amplitude of the pulses, a pulse width of the pulses, or a frequency of the pulses. In one example, the frequency is 10 kHz or less. In one example, the frequency is 1 kHz or less. In one example, the amplitude comprises a constant current amplitude. In one example, the control circuitry is further configured to determine an activity of the patient or to receive information indicative of an activity of the patient. In one example, the control circuitry is further configured to adjust the first duration of the single bolus in accordance with the determined activity or the information indicative of the activity. In one example, the stimulation parameters are determined in accordance with the determined activity or the information indicative of the activity. In one example, the control circuitry is programmed with a lockout period, wherein the control circuitry is further configured to transmit instructions to cause the implantable stimulator device to immediately provide the single bolus of stimulation to the neural tissue only if a second duration between the first time and a preceding bolus is equal to or longer than the lockout period. In one example, the control circuitry is further configured to schedule at least one other bolus after the single bolus in accordance with the lockout period.

A method is disclosed for providing stimulation to a patient using an implantable stimulator device and an external device in communication with the implantable stimulator device, comprising: determining stimulation parameters for the patient, wherein the stimulation parameters provide sub-perception stimulation pulses to address a symptom of the patient, receiving a first input at the external device to program a first duration, receiving from the patient at a first time a second input at a graphical user interface of the external device to immediately provide a single bolus of stimulation, and providing, using the implantable stimulator device, the single bolus to neural tissue of the patient for the first duration, wherein the single bolus comprises a plurality of periodic sub-perception stimulation pulses formed in accordance with the stimulation parameters.

In one example, the neural tissue comprises a spinal cord of the patient. In one example, the first duration of the single bolus is 3 minutes or longer. In one example, the stimulation parameters comprise one or more of an amplitude of the pulses, a pulse width of the pulses, or a frequency of the pulses. In one example, the frequency is 10 kHz or less. In one example, the frequency is 1 kHz or less. In one example, the amplitude comprises a constant current amplitude. In one example, the method further comprises determining an activity of the patient. In one example, the first duration of the single bolus is adjusted in accordance with the determined activity. In one example, the stimulation parameters are determined in accordance with the determined activity. In one example, the activity of the patient is determined using an activity sensor. In one example, the activity sensor is within the implantable stimulator device. In one example, information concerning the single bolus is transmitted to the implantable stimulator device from the external device. In one example, the graphical user interface is programmed with a lockout period, further comprising immediately providing the single bolus of stimulation to the neural tissue only if a second duration between the first time and a preceding bolus is equal to or longer than the lockout period. In one example, the method further comprises scheduling at least one other bolus after the single bolus in accordance with the lockout period.

BRIEF DESCRIPTION OF THE DRAWINGS

FIG. 1 shows an Implantable Pulse Generator (IPG) useable for Spinal Cord Stimulation (SCS), in accordance with the prior art.

FIG. 2 shows an example of stimulation pulses producible by the IPG, in accordance with the prior art.

FIG. 3 shows use of an External Trial Stimulator (ETS) useable to provide stimulation before implantation of an IPG, in accordance with the prior art.

FIG. 10 shows an algorithm for determining and monitoring bolus-mode stimulation.

FIG. 11 shows an algorithm for preemptively issuing a bolus of stimulation.

FIGS. 16A and 16B show an algorithm operable on an external device for determining an optimal bolus program for a patient.

DETAILED DESCRIPTION

Figure 4:
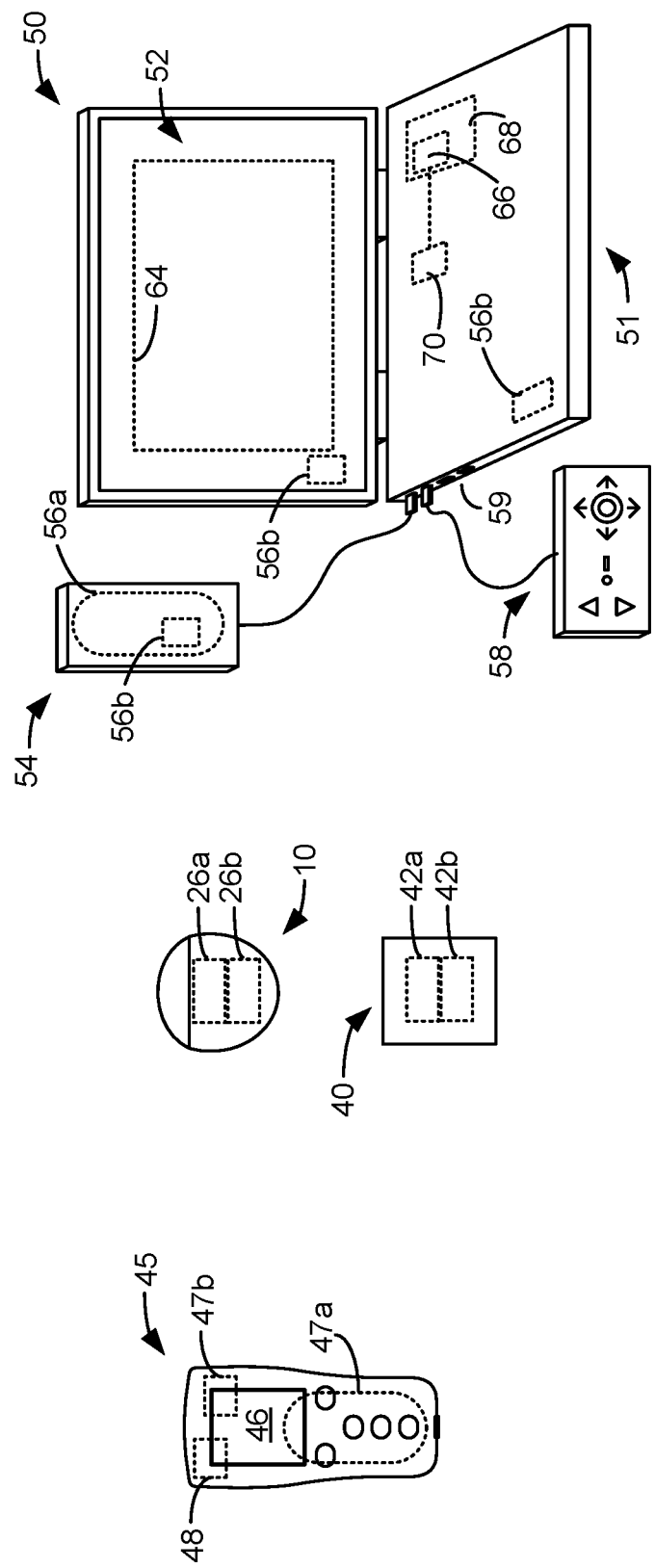
FIG. 4 shows various external devices capable of communicating with and programming stimulation in an IPG and ETS, in accordance with the prior art.

Generally, when a patient has been identified as a candidate for neuromodulation therapy, such as spinal cord stimulation (SCS), the patient receives one or more surgically implanted electrode leads (such as leads 15, FIG. 1). The leads may then be connected to an external trial stimulator (ETS 40, FIG. 4), which allows the patient and his clinician to experiment with different stimulation parameters to try and find a stimulation program that alleviates the patient's symptoms (e.g., pain). If the trial stimulation proves successful, the patient may receive a fully implanted IPG (10, FIG. 1). The patient will typically also receive an external controller (45, FIG. 4), which may be programmed with one or more stimulation programs comprising the parameters that have been determined to be most effective. The external controller allows the patient to select the stimulation programs and also allows them to control various parameters of their therapy, such as stimulation intensity, duration, etc. Under current paradigms, the patient is simply released and they can self-administer therapy at will without returning to the physician for review of effectiveness or follow-up.

The inventors have recognized deficiencies with this treatment paradigm. For one, simply releasing the patient without further scheduled follow-ups may be a missed opportunity for further evaluation and optimization of the patient's therapy. This is in contrast to typical pharmaceutical treatment regimens in which a clinician prescribes a finite number of doses of a drug and requires a follow-up visit to refill the prescription.

Another problem with the present SCS treatment paradigm of allowing the patient the unfettered ability to self-medicate is that the patient may overuse stimulation and develop a tolerance to their stimulation. Overstimulation can reduce the effectiveness of therapy even in the absence of other side effects. A patient may increase the frequency and/or intensity of their stimulation in an effort to compensate for a decrease in the effectiveness of their therapy. But such increases in stimulation can actually negatively impact the patient's therapy because they accelerate the rate at which the patient develops a tolerance to the stimulation. An ideal system would enable a clinician to manage the use of stimulation so that the patient does not overuse the stimulation and reduce the therapy effectiveness.

Disclosed herein are systems and methods that enable a clinician to prescribe a set amount of stimulation that a patient can receive before requiring the patient to seek a further prescription for additional stimulation. According to some embodiments, the prescribed amount of stimulation can be programmed into the patient's external controller or into the IPG. The system may track the amount of stimulation used. The user interface of the external controller may include an indication of the amount of prescribed stimulation remaining. When the patient has used all of the prescribed stimulation, the patient may be directed to make an appointment for a follow-up visit with their clinician to obtain a "refill" for their stimulation prescription. According to some embodiments, the patient's external controller may be an internet connectable device, in which case, the external controller may be configured to send a message to the clinician indicating that the patient has used all of their prescribed stimulation so that the clinician can proactively contact the patient to arrange an appointment.

Figure 7:
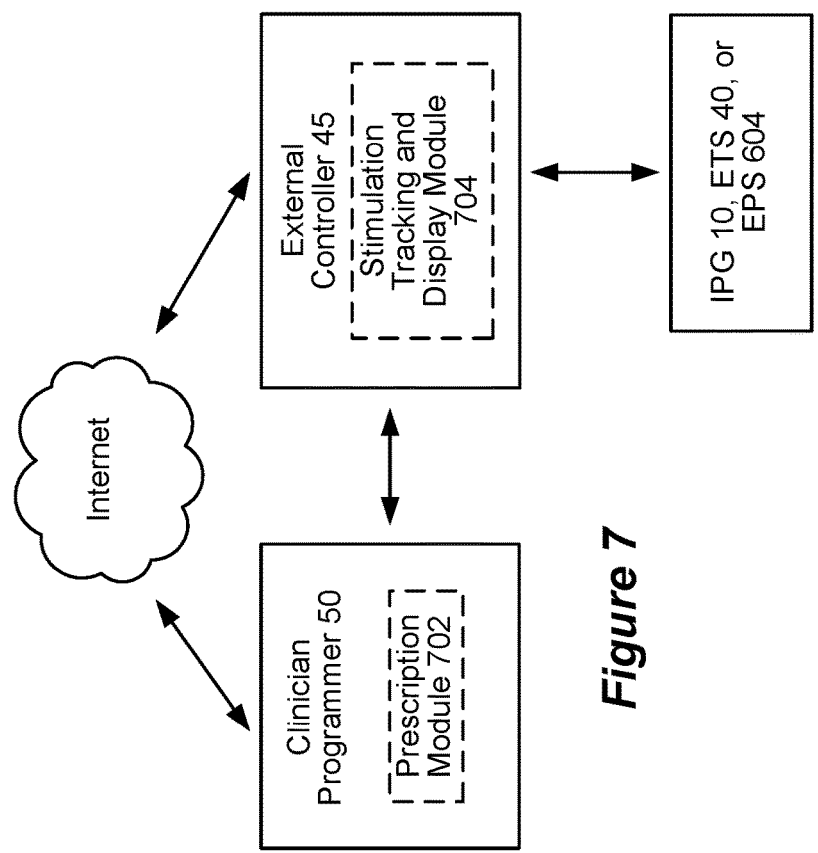
FIG. 7 shows a system for providing a prescribed amount of stimulation.

FIG. 7 illustrates a system 700 for prescribing and monitoring stimulation therapy. The system comprises a clinician programmer 50, which includes the functionality described above. In addition, the clinician programmer 50 comprises one or more therapy prescription modules 702, which are configured to aid the clinician in prescribing an amount of stimulation therapy. The therapy prescription module(s) 702 may be implemented as instructions embodied within non-transitory computer readable media associated with the clinician programmer 50 and executable by processing resources (i.e., one or more microprocessors and/or control circuitry) of the clinician programmer. Such execution configures the clinician programmer to perform the functionality of the prescription module 702, which is described in more detail below.

Figure 6:
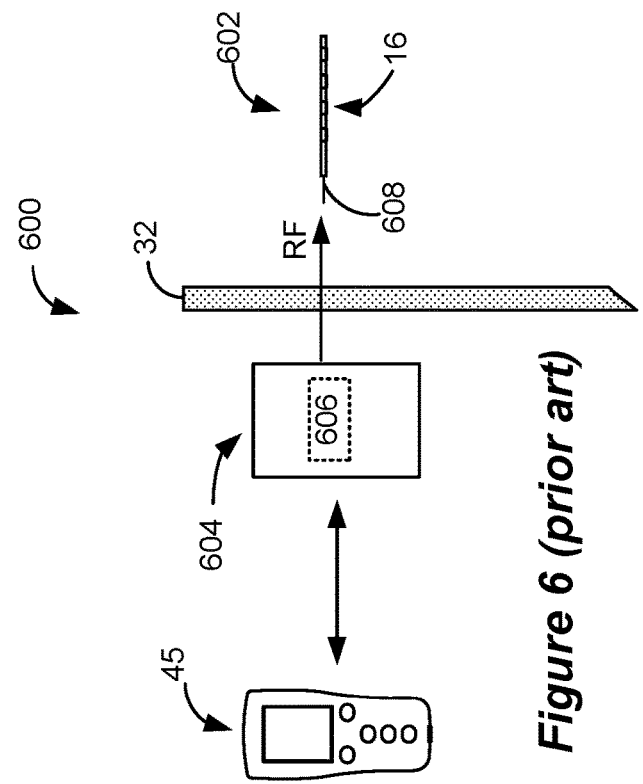
FIG. 6 shows an alternative configuration of an SCS system using an external power supply.

The clinician programmer is configured to transmit the stimulation prescription to the patient's external controller 45 or to the patient's IPG 10. The patient's external controller 45 may have all of the functionality described above for controlling the patient's IPG 10 (FIGS. 1, 3, and 4), ETS (FIG. 4), and/or EPS 604 (FIG. 6). In the illustrated embodiment, the external controller is configured with a stimulation tracking and display module 704 that is configured to receive the stimulation prescription from the clinician programmer 50, track the amount of stimulation used, and display an amount of stimulation remaining on the prescription to the patient. The stimulation tracking and display module 704 may be implemented as instructions embodied within non-transitory computer readable media associated with the external controller 45 and executable by processing resources (i.e., one or more microprocessors and/or control circuitry) of the external controller. Such execution configures the external controller to perform the functionality of the stimulation tracking and display module. According to other embodiments, the prescription and the tracking of the stimulation used may be performed in the IPG, which can communicate the prescription/use information to the patient's external controller for display.

As the prescribed stimulation is used up, the patient may be prompted to schedule an appointment with their clinician to receive a further prescription for additional stimulation. As mentioned above, if the patient's external controller 45 is an internet-connected device, the external controller may be configured to send a notice to the clinician indicating that the patient's prescribed amount of stimulation is depleted or approaching depletion so that the clinician can proactively contact the patient to schedule an appointment. In embodiments wherein the IPG tracks the prescription, the IPG may be configured to send a notice to the patient's personal phone or other computing device (via a Bluetooth connection, for example) informing them that the prescription is depleted or nearing depletion. According to some embodiments, the clinician programmer 50 may be configured to refresh the prescription via an internet connection.

Figure 8:
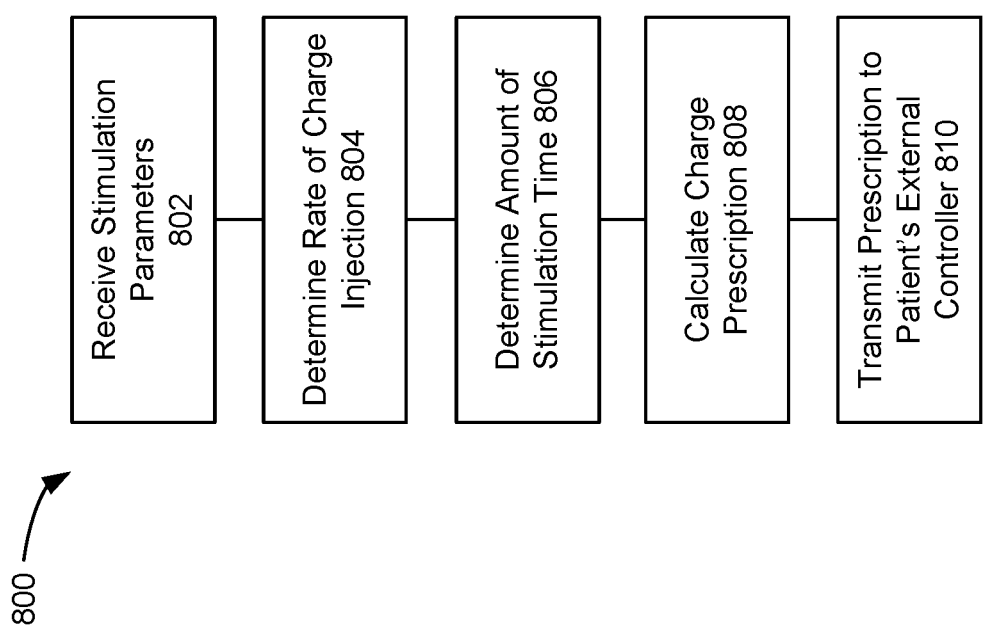
FIG. 8 shows an algorithm for determining a prescription for an amount of stimulation.

According to some embodiments, the prescribed amount of stimulation can be set as a total amount of actively delivered charge. FIG. 8 illustrates an example of an embodiment of an algorithm 800 that a clinician may use to determine and prescribe an amount of total charge to prescribe for a patient's therapy. The algorithm 800 may implemented as a program in the clinician programmer 50 (FIG. 4), for example, as a component of a prescription module 702 (FIG. 7). The algorithm assumes that the clinician and patient have determined one or more stimulation programs that are expected to be beneficial for the patient. The process of determining appropriate stimulation programs may be referred to as a fitting process.

At step 802 of the algorithm, the algorithm receives the stimulation parameters for the one or more programs that have been determined during the fitting process. For example, assume that the clinician has determined that the patient experiences pain relief when the patient is stimulated using a simple biphasic stimulation waveform, such as the waveform illustrated in FIG. 2. Assume that the waveform has a frequency of 100 Hz, an amplitude of 3 mA, and a pulse width of 100 μs. All of those parameters are provided to the algorithm at step 802. Of course, the stimulation program could be more complex, for example, involving complex pulse shapes, pulse patterns, and the like. Moreover, multiple programs may be determined during the fitting process. But for simplicity, a single simple biphasic waveform is considered here.

At step 804 the algorithm analyzes the stimulation waveforms contained in the defined stimulation program and calculates the rate of charge injection into the patient (i.e., the amount of actively driven charge provided as a function of time) when executing the stimulation program. For example, the stimulation parameters listed above would nominatively pass 0.108 Coulombs of charge per hour when executing the stimulation program.

At step 806 the algorithm receives input indicating an amount of time that stimulation should ideally be applied before the patient returns for a follow-up visit. For example, assume that the clinician believes that the patient should generally applying stimulation for 12 hours per day and the clinician would like for the prescription to be adequate for six months, after which, the patient should return for a follow-up visit. The clinician would enter those time parameters into the user interface of the clinician programmer, for example, as part of the prescription module 702 (FIG. 7).

At step 808 the algorithm calculates a charge prescription. In this simple example, the calculation is relatively straight forward. The values of the programmed stimulation parameters—amplitude, frequency, and pulse width—provide actively driven charge at a rate of 0.108 Coulombs per hour. That rate correlates to 1.3 Coulombs per day if the patient applies stimulation for 12 hours per day, which further correlates to 232 Coulombs over six months (180 days). Thus, the prescription will be calculated as 232 Coulombs, based on the parameters provided by the clinician. It should be appreciated that since the algorithm has access to the stimulation waveform program and the relevant stimulation parameters, the algorithm can be configured to calculate the actively driven charge for generally any duration of stimulation, even for complex waveforms.

At step 810, the calculated charge prescription can be transmitted from the clinician programmer to the patient's external controller. It should be noted that while the illustrated algorithm 800 computes a stimulation prescription based on Coulombs of charge, neither the clinician nor the patient may be interested in the absolute value of Coulombs, per se. Instead, the clinician can simply prescribe stimulation based on the particular stimulation parameters, the amount of stimulation per day, and the ideal length of time before a follow-up appointment. Given those data points, the algorithm 800 calculates a "charge prescription." It should also be noted that the prescription may be determined on the basis of total energy or some other metric that relates to an amount of stimulation. For example, the clinician may prescribe stimulation on the basis of time, time per day, or boluses of stimulation, which is discussed in more detail below. The prescription module 702 executed on the clinician programmer may be configured with different options for allowing the clinician to prescribe stimulation.

Figure 9:
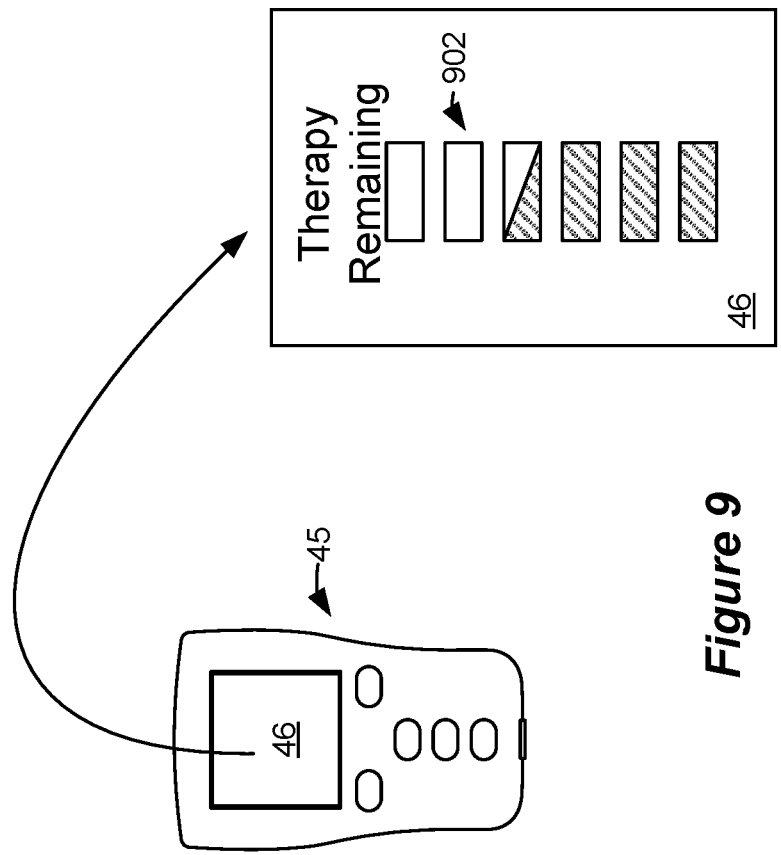
FIG. 9 shows a user interface for tracking prescribed stimulation.

FIG. 9 illustrates an embodiment of an external controller 45 having a display 46. The external controller may comprise a stimulation tracking and display module 704 (FIG. 7) configured to receive the stimulation prescription from the physician controller and to account for the amount of charge used during stimulation. The amount of charge remaining for the patient's prescription may be displayed on the display 46 of the patient's external controller. For example, in the illustrated embodiment, the external controller presents a gauge 902 indicating the amount of therapy remaining on the prescription. As the patient uses their SCS system their external controller can track the amount of charge used and may display the amount of charge remaining on the prescription (either as charge or some variable related to charge). When the patient's prescribed charge is depleted or approaching depletion, they may be prompted to schedule a follow-up appointment with the clinician. The patient may use their prescribed amount of stimulation at a faster rate than anticipated, for example, by applying stimulation more frequently or by using a greater amplitude or pulse width. In that case, the patient will be prompted to schedule a follow-up sooner than the anticipated six months. This may afford the patient and clinician to explore reasons that the patient is requiring more stimulation than anticipated.

According to some embodiments, stimulation may be provided in discreet chunks of stimulation, referred to as a "bolus" of stimulation. A bolus of stimulation may be thought of as analogous to a single dose of stimulation, similar to a dose of a pharmaceutical agent. For example, a bolus may comprise stimulation for a first period of time, such as 10 minutes of stimulation (or 30 minutes, or 1 hour, etc.). After a bolus is issued further stimulation is not provided until another bolus is issued. Typically, the time period between boluses (i.e., a second period of time) is on the order of at least minutes, or hours, for example. For example, according to some embodiments, the second period of time may be thirty minutes to twelve hours. However, according to some embodiments, a patient could issue themselves another bolus immediately following a first bolus, just as patient could take a second dose of a pharmaceutical immediately following a first dose. Preferably, a bolus comprises a number of periodically-issued pulses at a set frequency.

It has been observed that some patients respond well to bolus mode treatment. A patient may initiate a bolus of stimulation when they feel pain coming on. Some patients experience extended pain relief, up to several hours or more, following receiving a bolus of stimulation. According to some embodiments, a clinician may prescribe stimulation therapy based on a number of boluses of stimulation. To draw an analogy to a pharmaceutical prescription, a clinician might prescribe a given number of boluses of stimulation to a patient per day for a certain duration. For example, a clinician might prescribe five 30-minute boluses of stimulation per day for three months, after which the patient returns to the clinician for a follow-up evaluation.

Figure 5:
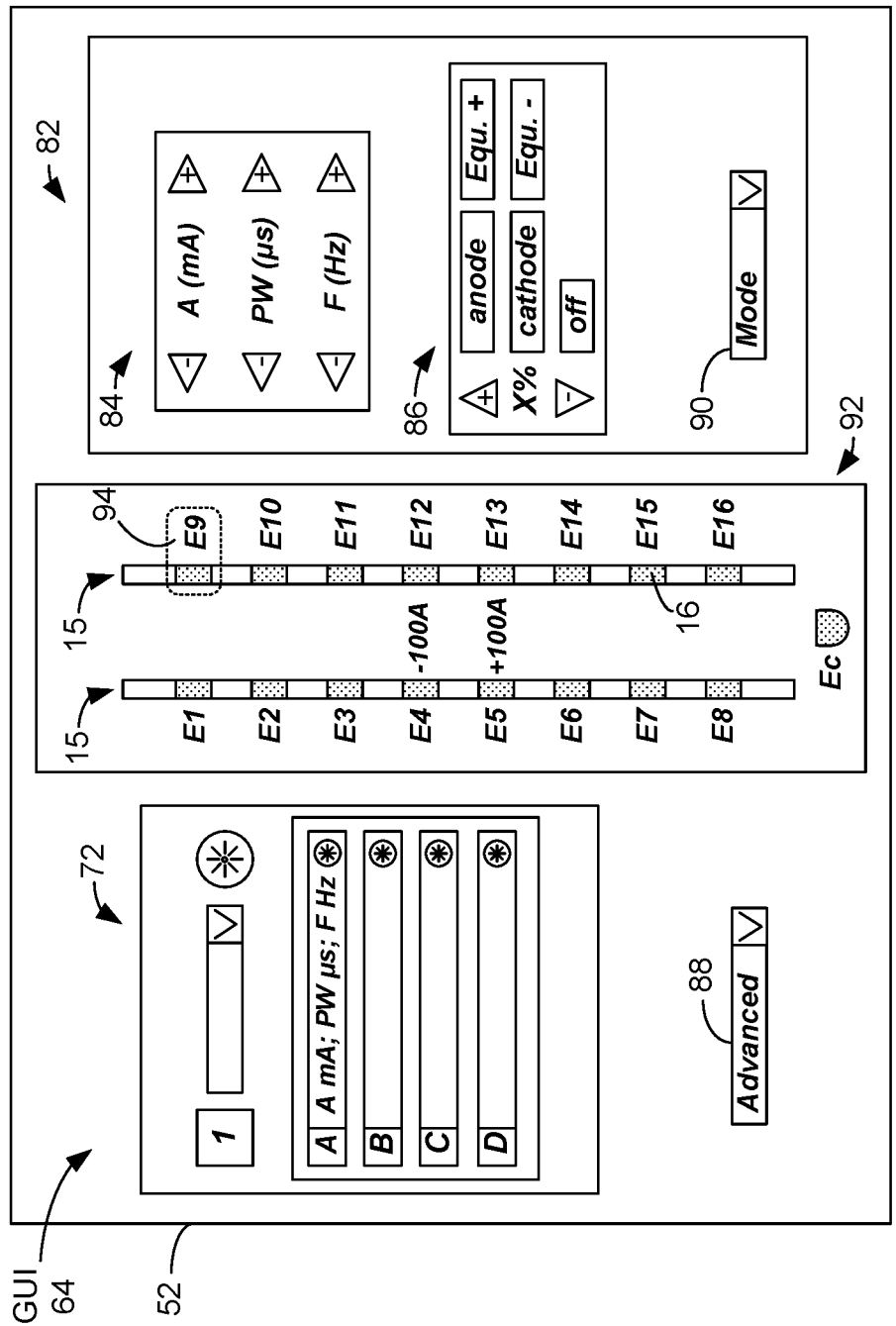
FIG. 5 shows a Graphical User Interface (GUI) of a clinician programmer external device for setting or adjusting stimulation parameters, in accordance with the prior art.

FIG. 10 illustrates an example of a method 1000 of determining and prescribing a bolus mode treatment. At step 1002, appropriate stimulation parameters are determined for the patient. This process is generally done in a fitting session with the aid of a clinician programmer 50 (FIGS. 4, 5, and 7), as described above. Assume that, during the fitting process, the clinician has determined one or more stimulation programs that alleviate the patient's pain and also assume that the clinician believes that the patient may respond well to bolus mode treatment. Having determined optimum stimulation parameters, the patient may be released with an implanted IPG (or ETS or EPS) and their external controller 45 to determine an appropriate time period corresponding to a bolus of stimulation. For example, the stimulation tracking and display module 704 in the patient's external controller may be programmed with a bolus algorithm configured to help the patient and clinician determine an appropriate bolus of stimulation. The goal is to determine a time period of stimulation that achieves long-lasting pain relief. When the patient experiences the onset of pain, they may activate a trial bolus. For example, a trial bolus may comprise 5 minutes of stimulation using the patient's optimum stimulation parameters. The patient will receive a bolus of stimulation, after which the stimulation will terminate. The patient may then be asked to periodically rate their pain relief (for example, every hour after the administration of the trial bolus) using the interface of their external controller. Over a period of days or weeks, different time periods of stimulation may be tried to determine a minimum time period that provides the longest-lasting pain relief. Various optimization criteria may be used for making the determination of an optimum bolus, depending on the patient's and the clinician's preferences. Alternatively, the clinician may simply decide what time period of stimulation will constitute a bolus of stimulation at step 1004.

Having determined an appropriate stimulation duration corresponding to a bolus of stimulation, the patient may receive a prescription for a number of boluses (step 1006). According to some embodiments, the patient may return to their clinician following the bolus determination step (step 1004) so that the clinician can program the patient's external controller with a prescription for a given number of boluses. According to some embodiments, if the patient's external controller is an internet-connected device, the patient may not need to return to the clinician. Instead, the patient's external controller may transmit the bolus duration to the clinician programmer via an internet connection and the clinician programmer may transmit the bolus prescription to the patient's external controller via the internet connection. Once the patient's external controller is programmed with a bolus prescription, the external controller can monitor the number of boluses used (Step 1008). The number of boluses remaining on the patient's prescription may be displayed on the external controller. Once the patient has used the prescribed number of boluses, the patient may be prompted to schedule a follow-up visit with the clinician.

It should be noted that, according to some embodiments, the clinician may simply prescribe a certain stimulation duration as a bolus without using an algorithm such as the algorithm 1000. For example, the clinician may simply decide that a bolus of stimulation will correspond to ten minutes of stimulation. Alternatively, according to some embodiments, the patient's external controller may be programmed with an algorithm that helps the patient determine an appropriate bolus of stimulation without approval of the clinician. For example, the patient's external controller may be programmed with a bolus calibration duration, for example, two weeks, during which the patient is prompted to rate or rank therapy using different bolus durations. After the calibration duration, the external controller considers the determined optimum duration of stimulation as a bolus of stimulation. The external controller may then begin tracking the number of boluses remaining for the patient's prescription. For example, the GUI of the external controller may inform the patient that they have x of y boluses remaining.

According to some embodiments, the patient's external controller may be programmed with one or more algorithms that attempt to optimize when a bolus of stimulation should issue. When the algorithm determines that a bolus should be issued, the patient's external controller may alert the patient to administer themselves a bolus of stimulation. Such an embodiment may be particularly useful for patients using an RF system (i.e., a system without an implanted IPG). A patient using such a system can receive a notice or alert when it is time to receive a bolus of stimulation and the patient can then arrange their external power supply (EPS) appropriately an administer themselves a bolus. Alternatively, a patient using a system with a traditional IPG can use their external controller to cause the IPG to issue a bolus of stimulation when they receive an alert that it is time to issue a bolus. According to some embodiments, the external controller may simply instruct the IPG to issue a bolus automatically without the patient instructing the external controller to so. According to some embodiments, the patient may receive an alert on their personal computing device, such as a personal phone, that it is time to take a bolus.

FIG. 11 illustrates an example of an algorithm 1100 for predicting when a bolus should issue. The algorithm 1100 comprises a "training period" during which the algorithm attempts to correlate one or more "pain predictors" with instances that the patient issues themselves a bolus. The pain predictor is a predictor indicative of a need for stimulation. Examples of pain predictors may include the time of day, the weather, the patient's activity level, or one or more physiological parameters of the patient, such as heartrate, blood pressure, posture, or the like. For example, during the training period the algorithm may determine that the patient tends to issue themselves a bolus at certain times during the day. The algorithm may therefore determine that those are the times of day that the patient tends to experience pain. Likewise, the algorithm may determine that the patient tends to administer a bolus when they transition from sitting to standing, or vice-versa. Such postural changes may be detected using measured evoked compound action potentials (ECAPs) or other sensed neural responses, as described in PCT Int'l Patent Application Publication WO2020/251899. Alternatively (or additionally), postural changes and/or patient activity level may be determined using accelerometers. Physiological parameters, such as heartrate, blood pressure, and the like may be determined using one or more physiological sensors associated with the patient. According to some embodiments, pain predictors such as activity level, weather, posture, and the like, may be determined based on patient input, for example, via an application running on their external controller or other external device in communication with their external controller. Alternatively, to determine weather conditions, the patient's external controller (or other external device in communication with the external controller) may be configured to obtain weather information via internet weather data. The training period may be a few days or a few weeks, for example.

Once the training period is concluded, the algorithm may proceed to a directed therapy or automatic therapy regime wherein the algorithm monitors for one or more of the pain predictors. When a pain predictor is detected the algorithm may either instruct the patient to preemptively issue themselves a bolus or may automatically issue the patient a bolus without patient input. As mentioned above, embodiments wherein the patient is instructed to issue themselves a bolus are particularly useful for patients with an RF system that does not use an implanted IPG.

According to some embodiments, the patient may be prompted for feedback rating the effectiveness of the attempted therapy programs, for example, by selecting a rating on the user interface of their external controller. Based on the patient feedback, the algorithm may attempt to optimize the algorithm.

Figure 12A:
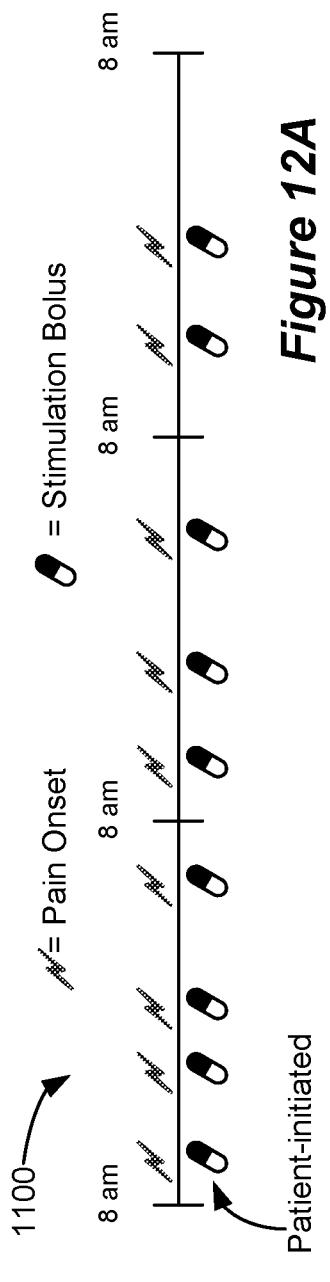
FIGS. 12A-12C show the use of an algorithm for preemptively issuing a bolus of stimulation.
Figure 12B:
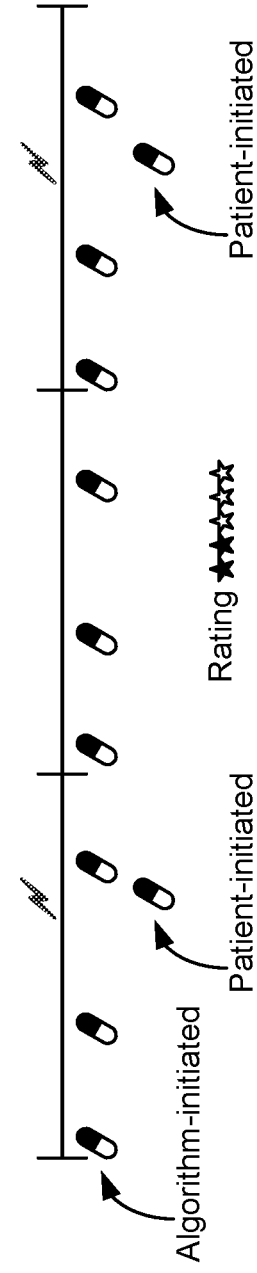
Figure 12C:
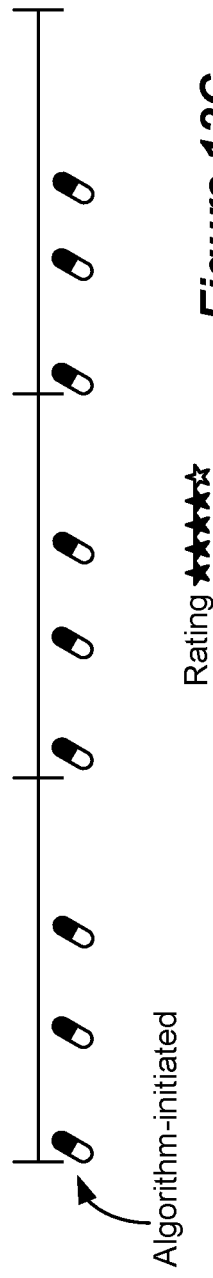

FIGS. 12A-12C illustrate an example of the algorithm 1100 for determining when to preemptively issue a bolus of stimulation. The example algorithm 1100 illustrated in FIG. 12A-12C uses the time of day as the pain predictor and also uses patient feedback to optimize the algorithm. FIG. 12A illustrates a training period where the patient self-administers a bolus (represented by a capsule in FIGS. 12A-12C) each time they perceive the onset of pain (represented by a lighting bolt). According to some embodiments, an algorithm may track the times that the patient issues themselves a bolus and then attempt to preemptively issue a bolus before the patient experiences pain onset. Notice in FIG. 12A that the patient's pain onset events are weighted more heavily to the early part of the day. Assume that the algorithm 1100 has tracked the three days of therapy illustrated in FIG. 12A. FIG. 12B illustrates an attempt by the algorithm to preemptively issue boluses of therapy over a three-day period based on the boluses that the patient administered in FIG. 12A. For example, in FIG. 12A, the patient, on average, administered three boluses per day. So, in FIG. 12B, the algorithm 1100 automatically provides those boluses each day at time periods that best match those in FIG. 12A. The patient can continue to self-administer boluses and the algorithm 1100 can continue to optimize the timing of automatically providing boluses. For example, on days one and three, the preemptively issued boluses of were not sufficient to completely curtail the patient's pain and the patient had to self-administer an extra bolus on those days. In FIG. 12B, the patient has rated the therapy two-out-of-five. In FIG. 12C, the algorithm has attempted to improve the therapy by issuing the third bolus earlier in the day, corresponding to the self-administered boluses. The patient has not had to self-administer a bolus of stimulation over a three-day period and has rated the therapy a four-out-of-five. The algorithm 1100 may thus determine that the timing determined in FIG. 10C may be used as ongoing therapy.

Bolus mode therapy may provide several advantages compared to traditional continuous therapy. For example, bolus mode therapy may decrease the chances that the patient overuses stimulation, thereby developing a tolerance to the therapy. Also, bolus mode therapy is particularly well suited for RF stimulation systems, such as described above with reference to FIG. 6. Since a bolus of stimulation is only applied for a finite duration of time, a patient using an RF system need only have access to their external power supply during the time they are receiving a bolus of stimulation.

Various aspects of the disclosed techniques, including processes implementable in the IPG or ETS, or in external devices such as the clinician programmer and/or the external controller can be formulated and stored as instructions in a computer-readable media associated with such devices, such as in a magnetic, optical, or solid-state memory. The computer-readable media with such stored instructions may also comprise a device readable by the clinician programmer or external controller, such as in a memory stick or a removable disk, and may reside elsewhere. For example, the computer-readable media may be associated with a server or any other computer device, thus allowing instructions to be downloaded to the clinician programmer system or external controller or to the IPG or ETS, via the Internet for example. The various algorithms described herein and stored in non-transitory computer readable media can be executed by one or more microprocessors and/or control circuitry configured within the relevant device, thereby causing the device to perform the steps of the algorithm(s).

The disclosed technique of providing stimulation in boluses has also shown to have benefits in providing sub-perception stimulation therapy to patients. As discussed in other applications, such as PCT Int'l Patent Application Publication WO2021/003290, which is incorporated herein by reference in its entirety, while Spinal Cord Stimulation (SCS) therapy can be an effective means of alleviating a patient's symptoms such as pain, such stimulation can also cause paresthesia. Paresthesia—sometimes referred to a "supra-perception" therapy—is a sensation such as tingling, prickling, heat, cold, etc. that can accompany SCS therapy. Generally, the effects of paresthesia are mild, or at least are not overly concerning to a patient. Moreover, experiencing paresthesia can be a reasonable tradeoff for a patient whose pain (neuropathic, nociceptive, and/or mechanical) has now been brought under control by stimulating neural tissue using SCS therapy. Some patients even find paresthesia comfortable and soothing.

Nonetheless, at least for some patients, SCS therapy would ideally provide complete pain relief without paresthesia—what is often referred to as "sub-perception" or sub-threshold therapy that a patient cannot feel. The '290 Publication explains different examples of how effective sub-perception therapy can be provided for a patient. In the examples of in the '290 Publication, sub-perception stimulation is typically provided at frequencies such as 10 kHz or less, or more preferably 1 kHz or less. Providing sub-perception stimulation at lower frequencies is preferred, as this is generally less power intensive, meaning that the battery in the IMD will last longer, or will not need to be recharged as frequently as when higher frequencies are used.

Figure 13A:
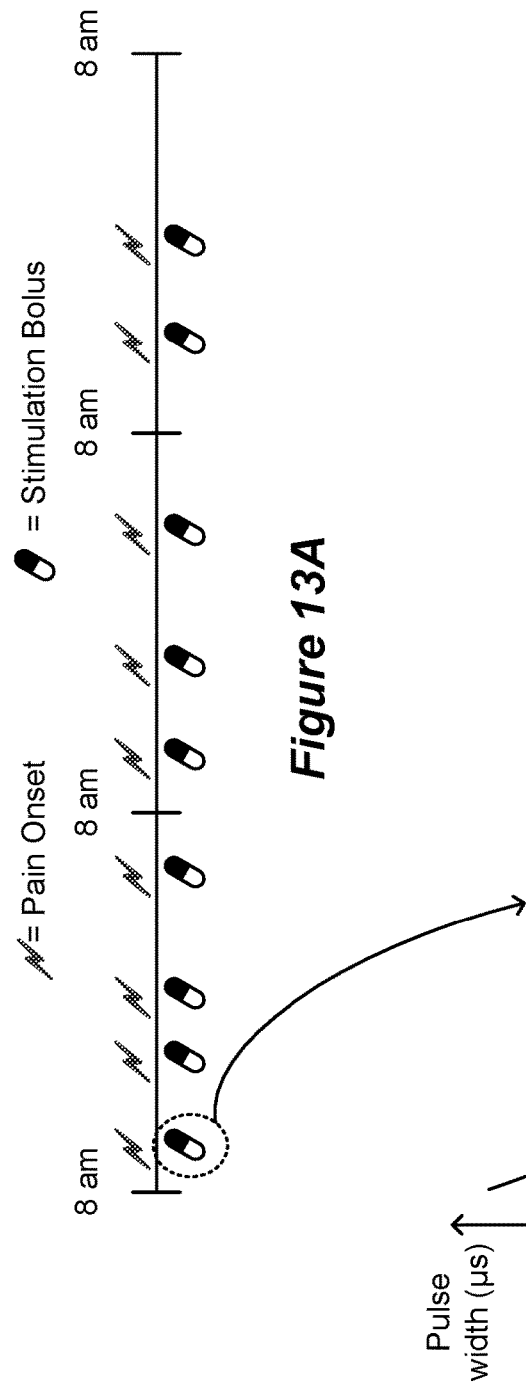
FIGS. 13A and 13B show use of bolus of simulation in the provision of sub-perception stimulation therapy.
Figure 13B:
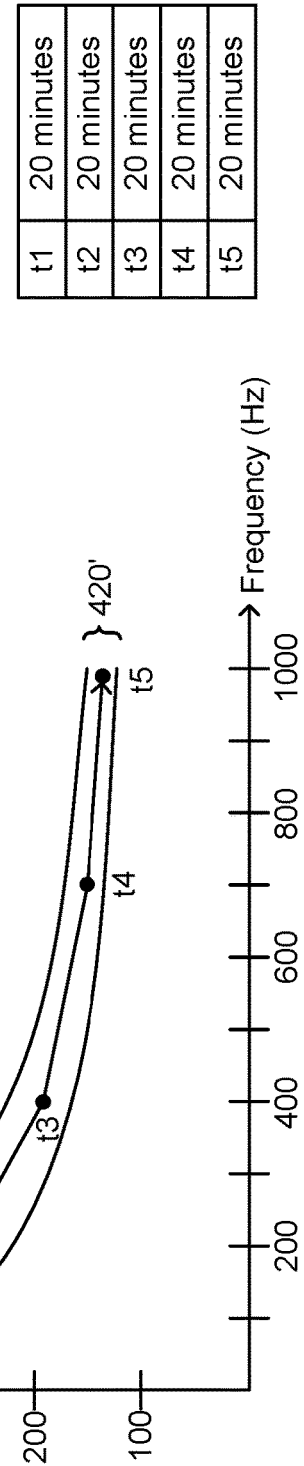

The '290 Publication provides an example in which boluses of sub-perception simulation are provided, which is shown here in FIGS. 13A and 13B. As shown in FIG. 13A and as in earlier examples, boluses are provided periodically, and for a set period of time, such as ten minutes, thirty minutes, one hour, two hours, or any other duration that is effective, with gaps of time where no stimulation is provided between the boluses. A patient may initiate a bolus of stimulation when they feel pain coming on, or these boluses may be administered automatically, as discussed earlier. Providing sub-perception stimulation in boluses can be beneficial because some patients experience extended pain relief, up to several hours or more, following receiving a bolus of stimulation. Furthermore, providing boluses of stimulation saves power in the IPG because simulation is not continuous, and also helps to prevent over-stimulation and habituation of the tissue, where the tissue becomes "used to" the stimulation rendering it less effective over time.

The sub-perception stimulation parameters used during each stimulation bolus can be adjusted, as shown in FIG. 13B. For example, the stimulation bolus shown is 100 minutes in length, and consists of five different time periods t1-t5, each lasting 20 minutes. In this example, one or more stimulation parameters (e.g., pulse width and frequency) are adjusted consistent with sub-perception stimulation parameters 420' determined to be optimal in the '290 Publication. In this example, these optimal stimulation parameters 420' comprise a relation between the frequency and the pulse width of the sub-perception stimulation pulses. However, other stimulation parameters, such as pulse amplitude, can also be determined as part of the optimal stimulation parameters 420'. In this example the sub-perception stimulation parameters are made to change during each bolus, consistently with the optimal stimulation parameters 420'. For example, during a first portion of the boluses (t1, 20 minutes), a relatively high pulse width and a relative low pulse frequency are used. During a next portion of the boluses (t2, 20 minutes), the pulse width is decreased while the frequency is increased. Again, this is just one example. Further, the sub-perception stimulation parameters used during the bolus need not change, but can instead be constant over the entire duration of each bolus.

Sub-perception stimulation therapy lends itself well to the prescription of stimulation in boluses because, as discussed in the '290 Publication, sub-perception therapy "washes in" relatively quickly, and "washes out" relatively slowly. "Wash in" refers to a time period before sub-perception therapy becomes effective in treating the patient's symptoms, such as pain, and can be as little as a matter of seconds or minutes. "Wash out" refers to a time period that sub-perception therapy remains effective in treating symptoms after stimulation has ceased, and can be as long as hours. Accordingly, it can be effective and beneficial to provide sub-perception stimulation in boluses, because each bolus can treat the patient quickly, and can remain effective even after the bolus ends and a next bolus is applied. Further benefits are had by providing sub-perception stimulation in boluses because stimulation is not provided in the time periods between boluses, which save energy and is more considerate of the IPG's battery. Providing sub-perception therapy in boluses also prevents overstimulation of the patient, and wards again tissue habituation.

Figure 14:
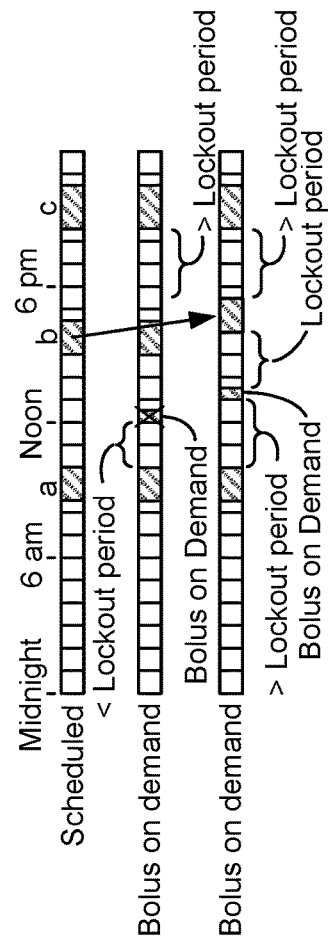
FIG. 14 shows a graphical user interface operable on an external device that can be used to schedule sub-perception therapy.

FIG. 14 shows an example of how sub-perception bolus therapy can be administered to a patient. Shown are various options that can be selected by the patient or clinician to set the duration of the boluses as well as the off-time between boluses. Various options are shown by which a patient or clinician can schedule bolus stimulation. This example is illustrated in the context of a GUI that can appear on the patient's external controller 45 or the clinician programmer 50, because as noted earlier either of these external devices can be used to adjust a patient's stimulation therapy. As noted earlier, the GUI can be rendered by execution of software stored in memory in the external device. These various options shown in FIG. 14 for prescribing bolus stimulation therapy can also be used for supra-perception therapy involving paresthesia, although focus is given on the provision of sub-perception therapy.

Option 500 allows the patient or clinician to enter relevant sub-perception stimulation parameters to be used during each bolus, such as the amplitude (A) of stimulation (e.g., in mA), the pulse width (PW) of the stimulation pulses, and the frequency (F) of such pulses. These stimulation parameters can be manually entered, and preferably can comprise optimal sub-perception stimulation parameters 420' determined in various manners disclosed in the '290 Publication. Option 501 can be selected to use such optimal stimulation parameters 420'. Note as taught by the '290 Publication that selection of option 501 may cause an algorithm to run to determine the optimal stimulation parameters 420' specifically for the patient. Because such details are described in the '290 Publication, they are not reiterated here. Although not shown, the stimulation parameters may be varied during each bolus, as just described with respect to FIG. 13B.

Option 502 allows the patient or clinician to specify bolus parameters, such as the on duration of the boluses (e.g., 30 minutes) and the off-time (e.g., 3.5 hours) between each of the boluses when no simulation is occurring. This option 502 may include a graphical that displays a time line of when the boluses will occur during the course of the day. For example, the graphic in FIG. 14 shows that the boluses as scheduled will occur from 3:30 am to 4:00 am, 7:30 am to 8:00 am, 11:30 am to noon, and so on at intervals of four hours. Bolus durations can be 3 minutes or longer, 10 minutes or longer, 30 minutes or longer, 1 hour or longer, 2 hours or longer, 3 hours or longer, or even longer. The duration of off times can be 30 minutes or longer, 1 hour or longer, 2 hours or longer, 5 hours or longer, or even longer.

Option 504 allows the patient or clinician to specify the issuance of boluses on a daily schedule, and more particularly allows for scheduling boluses of different durations and during different times depending on the day of the week. Such scheduling can be sensible, because a patient's stimulation needs may vary depending on his or her activities, which may vary during different days of the week. In this example, for the sake of simple illustration, the scheduling of bolus stimulation is the same for weekdays (Monday-Friday) and for weekend days (Saturday, Sunday). This is of course just one example, and each day of the week could also be individually and uniquely scheduled.

In this example, boluses are scheduled during periods when the patient is expected to be engaging in significant activity. For example, during weekdays, bolus stimulation is scheduled to occur from 7:30 am to 9:00 am, when the patient is waking up and preparing for work. At 9:00 am, this bolus stops, because the patient is now at work, and perhaps not as mobile. Again, because the stimulation can have a significant wash-out period, particularly when sub-perception therapy is used, it can be assumed that the patient will continue to experience therapeutic benefits for some time (past 9:00 am) even though stimulation has ceased. At noon, when the patient may again be more active (e.g., lunch time), another bolus can be administered, which may last to 1:30 pm. Even if the patient will not be active at this time, scheduling a bolus may be warranted because the wash-out period from the previous bolus has now expired. A next bolus is administered from 7:30 pm to 8:30 pm. Notice that this bolus may be of a shorter duration (one hour, compared to earlier boluses of 1.5 hours), because the need for sub-perception stimulation therapy may not be as significant at this time.

During weekend days, the administration of the boluses occurs at different times. For example, the patient may sleep in during these days, and hence the first daily bolus may be shifted out later in time, such as from 8:30 am to 10:00 am. A second bolus is also scheduled later in time, from 3:00 pm to 4:30 pm, as the patient may be shopping or engaging in other activities at this time. A third bolus is administered later in the day, and of a longer duration, from 8:30 pm to 10:30 pm. This may be sensible, as the patient may be out for the evenings, and thus needing more significant therapy during these times.

Option 506 allows a patient to self-administer a bolus of stimulation by selecting option 508. This can be useful, because pre-defined scheduling of boluses (e.g., options 502, 504) may not always be optimal, and a patient may experience symptoms during off periods between boluses. A demand bolus may be shorter than is otherwise scheduled (e.g., 30 minutes).

Option 510 allows for setting a lockout period, which in the example shown is set to 2.5 hours. The lockout period comprises a period of time during which a bolus cannot be prescribed, and such period is preferably referenced with respect to a preceding bolus. In the example shown, the lockout period starts from the end of a preceding bolus, although in other examples it may also start from the beginning of a preceding bolus. The lockout period prevents the patient from over stimulation, because it does not permit administration of another bolus until the lockout period has expired.

The lockout period option 510 may only be made accessible to the clinician; for example, setting this option may only occur upon entry of a clinician password. For example, the clinician may know from experience that the wash out period after the provision of a bolus comprises 3 hours, and therefore may set the lockout period accordingly, for example to a slightly smaller value of 2.5 hours. Once it is established, the lockout period 510 may comprise a global limitation on programming stimulation using the GUI, and may affect the ability to schedule bolus stimulation. For example, if the lockout period is set to 2.5 hours, the GUI may prohibit the entry of an off-time that is smaller than this in option 502. Likewise, when scheduling boluses using option 504, the GUI may prohibit setting a time period between the end of a bolus and the start of a next bolus that is smaller than the lockout period. Lastly, the lock period may also affect the ability of the patient to self-administer a bolus using option 506, as explained next.

The bottom of FIG. 14 shows operation of the lockout period, assuming that bolus stimulation has already been scheduled per option 504. Specifically shown is scheduling that occurs on Saturday, which scheduled the delivery of three boluses a, b, and c at different points in time during the day. Shown are two examples in which the patient attempts to self-administer an additional bolus using option 508. In the first example, bolus 'a' ends at 10 am, and the patient attempts to self-administer a bolus at noon. Because it has only been 2 hours since the end of bolus 'a', and because this time period is smaller than the 2.5 hour lockout period, the GUI will not allow this self-administered bolus. Although not shown, the GUI might notify the patient that the bolus will not be provided and the reasons why, and might even suggest to the patient that a bolus may not be self-administered until 12:30 pm when the lockout period has expired.

The lockout period may also affect subsequently scheduled boluses. In the next example, the patient attempts to self-administer an additional bolus at 1 pm. Because it has been 3 hours since the end of bolus 'a', and because this time period is greater than the 2.5 hour lockout period, the GUI will allow this self-administered bolus to be provided. However, this self-administered bolus will end at 1:30 pm, and a next bolus 'b' is scheduled to occur at 3 pm. Because this off period (1.5 hrs) would be less than the lockout period (2.5 hours), the GUI can reschedule bolus 'b' later in time consistently with the lockout period. Thus, bolus 'b' is rescheduled to begin at 4 pm instead of 3 pm. Rescheduling bolus 'b' may also affect bolus 'c', which may also need to be rescheduled in light of the prescribed lockout period. However, that is not the case in the illustrated example. Bolus 'b' as rescheduled will end at 5:30 pm, while bolus 'c' is scheduled to begin at 8:30. This leaves an off period between boluses 'b' and 'c' which is greater than the lockout period. Thus, bolus 'c' does not need to be rescheduled. Although not shown, operation of the lockout period may cause some previously scheduled boluses to be canceled, rather than rescheduled (e.g., pushed out) in time.

Figure 15:
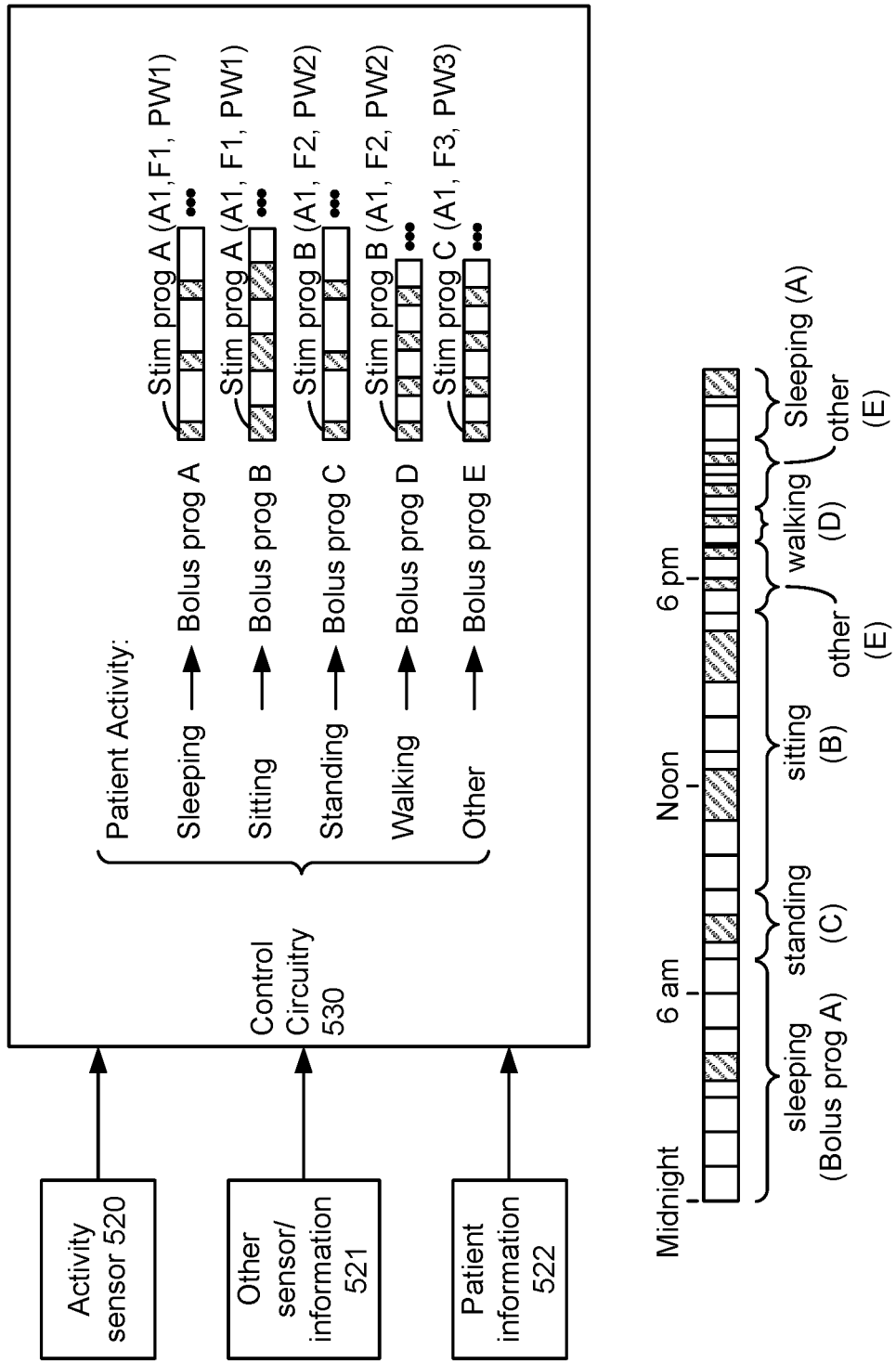
FIG. 15 shows how the IPG system can be used to detect various patient activities, and to execute a bolus program associated with a particular detected activity.

Bolus programming can also depend on patient activity, as shown in FIG. 15. Patient activity can be detected by an activity sensor 520. The activity sensor 520 may be associated with the patient's IPG or may comprise a wearable motion sensor able to communicate with the IPG, or the patient's external controller 45. An activity sensor 520 within the IPG may comprise an accelerometer or may comprise sensing circuitry associated with the IPG's electrodes. For example, and as mentioned earlier, ECAPs or other sensed responses to stimulation at the electrodes may be used to determine a patient's activity or posture. See, e.g., PCT Int'l Patent Application Publication WO2020/251899. Activity sensor 520 can also be within the patient's external controller 45. As used herein, a patent "activity" may comprise an activity the patient is engaged in (e.g., running, swimming, walking, etc.) or a particular patient posture (e.g., standing, prone, supine, sitting, etc.).

The activity sensor 520 can either determine the patient's activity, or can take measurements indicative of activity. These determinations or measurements can then be provided to control circuitry 530, which can determine the activity from the measurements if not already determined by the activity sensor 520. The control circuitry 530 can reside in the IPG, or within the relevant external device, and thus data received at the control circuitry 520 from the activity sensor 520 can be received wirelessly or by a wired connection. For example, control circuitry 530 can comprise the control circuitry 48 in the external controller 45, or the control circuitry 70 in the clinician programmer 50. The control circuitry 530 can also be associated with the stimulation circuitry 28 in the IPG. This is because either the IPG's control circuitry or the external device's control circuitry can be used to program boluses that the patient should receive in light of the patient activity being detected. For example, if the control circuitry 530 is within the IPG, the control circuitry will receive the activity data from the activity sensor by wired connection (if the activity sensor 520 is within the IMD) or wirelessly (if the activity sensor 520 is outside the IPG), and can adjust the bolus programming accordingly. If the control circuitry 530 is within an external device such as the patient external controller 45, the control circuitry can again receive the activity data from the activity sensor by wired connection (if the activity sensor 520 is within the external device) or wirelessly (if the activity sensor 520 is in the IPG or comprises a different wearable sensor), and can adjust the bolus programming accordingly by wirelessly programming the IPG. In the example shown in FIG. 15 it is assumed that relevant patient activities can comprise sleeping, sitting, standing, walking, or some other undetermined activity, although this listing of activities is merely an example.

The control circuitry 530 can, in the various manners just described, program the IPG (its stimulation circuitry 28, FIG. 1) with a bolus program appropriate for the detected patient activity. In the example shown in FIG. 15, there are five bolus programs (A-E) which are respectively associated with the patient activities of sleeping, suiting, standing, walking, and other. Preferably, each of the bolus programs provide some sort of schedule for the application of boluses to the patient. In the examples shown, this schedule is dictated by a bolus duration and an off-time, similar to what was described earlier in conjunction with option 502 (FIG. 14). However, each of the bolus programs can set the bolus on and off times differently. For example, the bolus programs may set a daily/weekly schedule for boluses, similar to what was described earlier in conjunction with option 504 (FIG. 14). Although not shown in FIG. 15, the patient may be able to self-administer boluses (508, FIG. 14) in addition to the boluses that are scheduled in each bolus program, and the duration (506) and lockout period (510) for such self-administered boluses may be adjusted appropriate for the activity in question. For example, activities that are more strenuous (e.g., walking) or involving higher degrees of patient movement may allow for self-administered boluses that are of longer duration, or that have shorter lockout periods, and thus options 506 and 510 can be modified accordingly. Indeed, the bolus programs associated with certain activities may have a lockout period of zero, meaning that boluses can be administered at any time regardless of when a preceding bolus was provided. The bolus programs may be pre-determined, and as taught in the '290 Publication may be pre-determined for the specific patient based on testing.

In addition, each bolus program may include or reference a stimulation program, i.e., the stimulation parameters such as amplitude, pulse width, and frequency that will be used to form the pulses during each of the boluses in the bolus program. For example, bolus program A uses stimulation program A, which uses A1, F1, and PW1 during each of the boluses. Bolus program B is different from bolus program A because it sets a longer duration for each of the boluses, but does not change the frequency at which boluses are administered. Bolus program B however also uses the same stimulation program A as does bolus program A. Bolus program C, when compared with bolus program A, does not change the duration or frequency of the boluses, but does use a different stimulation program B having a different pulse frequency (F2) and pulse width (PW2). Bolus program D uses this same stimulation program B, but causes the boluses to occur more frequently. Bolus program E uses the same bolus duration and frequency as does bolus program D, but uses a different stimulation program C. In short, each of the bolus programs can schedule and set the duration and timing of the boluses, and can provide for the use of different stimulation parameters during each of the boluses. When the stimulation provided by the bolus programs is sub-perception, the stimulation programs A-C may be determined in accordance with optimal stimulation parameters 420', as described in various manners in the above-incorporated '290 Publication. The bolus programs may be executed by the control circuitry in the IPG by providing relevant bolus and stimulation parameters to the IPG's stimulation circuitry 28 (FIG. 1).

The control circuitry 530 can receive other types of information as well, and can determine and use for the patient a corresponding bolus program accordingly. For example, the control circuitry 530 can receive information from other sensors or information sources 521 as well. Other sensor or information source 521 could for example sense certain conditions or vitals of the patient (e.g., EEG, EKG, blood pressure, temperature, etc.), and control circuitry 530 may select a bolus program in accordance with such sensed conditions or vitals. Other sensor or information source 521 may be remote from the patient, but can provide information to the control circuitry 530 via one or more communication links such as the Internet. For example, sensor 521 may comprise information about the weather, as gleaned from one or more weather sensors. It is known that the weather can affect a neurostimulation patient's symptoms, and thus that it may be warranted to change a patient's bolus program in accordance with different weather conditions. Control circuitry 530 can also receive information 522 about the patient or their disease process and select a bolus program accordingly. For example, patient information 522 may comprise the sex of the patient, their age, an indication of their particular disease process, the duration of that disease process, a duration of time since implantation, etc. In short, control circuitry 530 can choose a bolus program based on many different variables, although focus is given in FIG. 15 to the variable of patient activity for simplicity.

The bottom of FIG. 15 shows an example of the administration of boluses, and the provision of bolus programs, upon detection of certain patient activities. For example, detection determines that the patient is sleeping from midnight to 7 am, and thus runs bolus program A. From 7 am to 9 am the patient is standing, and thus runs bolus program C, and from 9 am to 5 pm the patient is sitting, and thus runs bolus program B. From 5 pm to 7 pm, and from 8 pm to 10 pm, the control circuitry 530 is unable to discern the patient's activity, perhaps because the patient is changing his activity rapidly. In this regard, the control circuitry 530 may change the bolus program on a slow time scale, and not necessarily whenever the patient's activity changes (e.g., for a negligible time). If the detected activity is changing on a fast time scale, the "other" bolus program E may be selected as a default, and notice that the frequency of the boluses may increase during such periods when the patient's activity cannot be exactly determined.

Figure 16A:
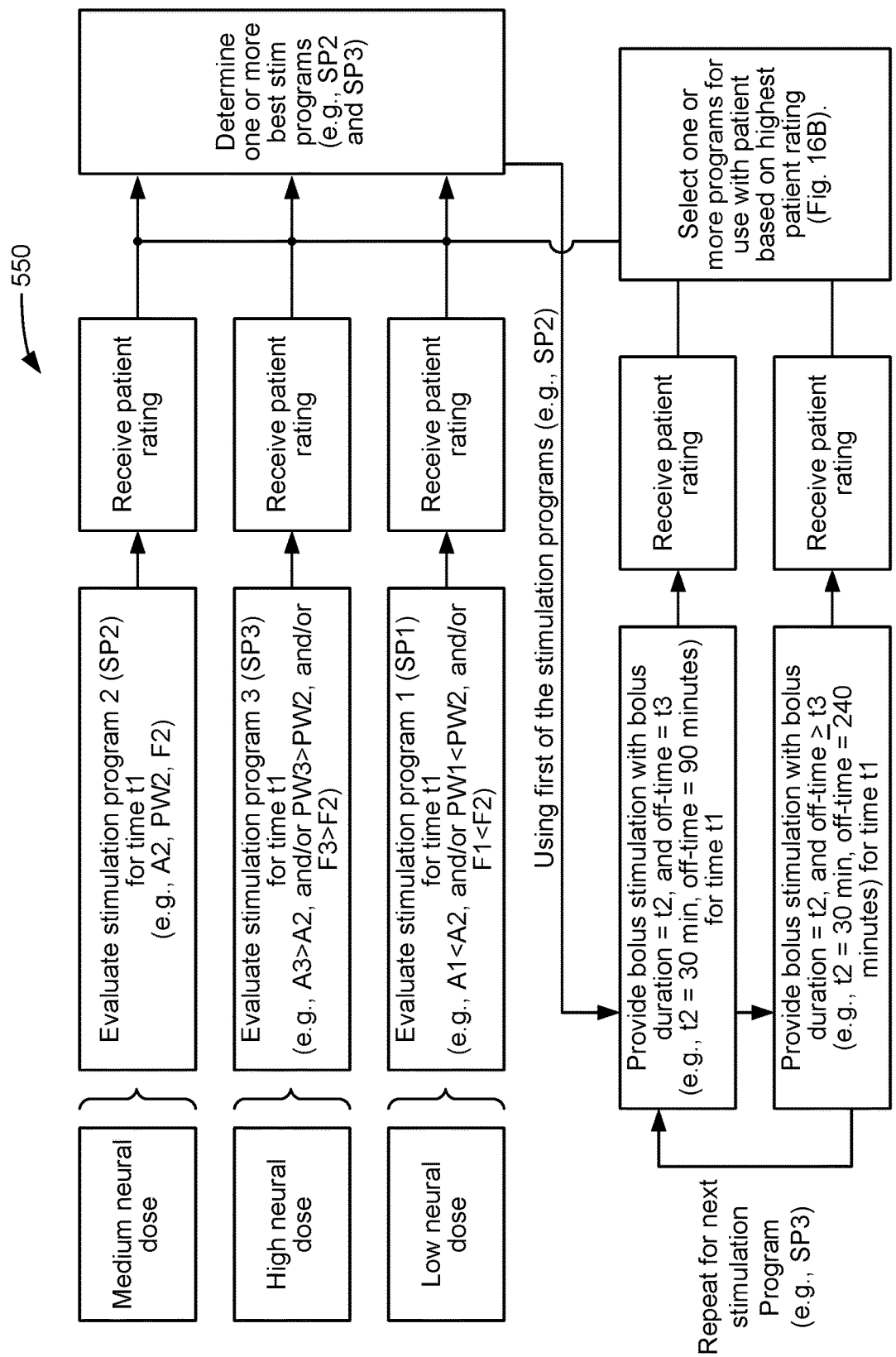

FIGS. 16A-16B shows a fitting algorithm 550 that may be used to determine one or more bolus programs for use with a patient. As will be described, algorithm 550 may vary bolus parameters (e.g., duration and off-period) and/or stimulation parameters (e.g., amplitude pulse width, and frequency) when determining an optimal bolus programs for the patient. It should be noted that algorithm 550 can also be used to determine optimal bolus programs for various patient activities, as just described with reference to FIG. 15. That being said, patient activity is not described with reference to FIG. 16A for simplicity. It is envisioned that algorithm 550 can be executed on an external device such as the external controller 45 or clinician programmer 50, although that external device may receive information for other components in the system.

Algorithm 550 preferably starts by determining an appropriate stimulation program for the patient. This can be viewed as establishing a neural dose for the patient, i.e., an amount of charge-per second that the patient will receive during each bolus. Neural dose may in one example be understood or calculated as the product of the amplitude, pulse width, and frequency, and algorithm 550 initially tries three such doses for the patient: a medium, high, and low dose. These dosages can set by different stimulation programs. For example, the medium dose comprises use of a stimulation program (SP2) having average values for amplitude (A2), pulse width (PW2), and frequency (F2). The high dose can comprise use of a stimulation program (SP3) that provides a higher neural dose, and so may have an amplitude (A3>A2), pulse width (PW3>PW2), and/or frequency (F3>F2) that is higher than that used during the medium dose. Similarly, the low dose can comprise use of a stimulation program (SP1) that provides a lower neural dose, and so may have an amplitude (A1<A2), pulse width (PW1<PW2), and/or frequency (F1<F2) that is lower than that used during the medium dose. Each of these doses—i.e., each of stimulation programs SP2, SP3, and SP1—can be tried for the patient for a time period t1, which may vary, but which may be about a day in length. At the end of each, the patient may rate how well that stimulation program addressed his symptoms, such as by entering rating information into his external controller 45, or into the clinician programmer 50. If necessary, such rating can be telemetered to the clinician programmer 50 upon which algorithm 550 may operate.

It is preferred that the stimulation programs tried for the patient in algorithm 550 comprise sub-perception programs, and thus comprise subsets of the optimal stimulation parameters 420' discussed earlier and in the '290 Publication. That being said, algorithm 550 may also consider and evaluate supra-stimulation programs as well.

The algorithm 550 can continue by determining one or more of the stimulation programs (doses) to be best for the patient based on the patient ratings. In the example of FIG. 16A, it is assumed that two best stimulation programs (e.g., SP2 and SP3) are determined for the patient, although only a single best stimulation program may be determined as well.

At this point, the algorithm 550 can attempt to determine best bolus parameters for use—such as bolus duration and off-time—with the previously-determined the best stimulation program(s). Thus, a first bolus duration (t2) and off-time (t3) are tried, using stimulation program SP2 during the boluses. Times t2 and t3 are variable but may equal 30 minutes and 90 minutes initially. A number of boluses are provided to the patient over a time period t1 (e.g., a day) long enough to provide the patient with a number of boluses and following off periods. The patient may then as before rate their experience with these parameters.

After this, and keeping the same stimulation program (SP2), the bolus parameters are varied. For simplicity, FIG. 16A only adjusts the off-time (t3), increasing it from 90 to 240 minutes. However, the bolus duration (t2) could also be varied. Again the patient rates these new parameters.

If more than one stimulation programs was earlier determined as a best candidate (e.g., SP3), the algorithm 550 can repeat, and provide this stimulation program in bolus form, and varying the bolus parameters as before. Again, the patient may rate each of the resulting bolus programs.

At the end of the algorithm 550, the various patient ratings can be considered to determine one of more bolus programs that are best for the patient, as shown in FIG. 16B. FIG. 16B show example patient ratings when stimulation is not provided with boluses (when medium, high, and low neural doses SP2, SP3, and SP1 are tried initially), and when stimulation is thereafter provided with boluses (using the two best stimulation programs SP2 and SP3). In the first example, SP2 and SP3 are rated highest (4), and thus those stimulation programs are tried while providing that stimulation according to various bolus parameters (i.e., various bolus durations and off-times). Providing boluses using SP2, with a bolus duration of 30 minutes and a off-time of 90 minutes yields the overall highest patient rating (5), suggesting that this bolus program would be best for the patient. Notice in this example that the patient prefers the use of bolus stimulation. This may mean that continuous stimulation (using SP2) is actually over stimulating the patient without any useful result (and while wasting power).

Notice that the algorithm 550 may also determine that continuous stimulation without the use of boluses may be best for the patient. This is illustrated in the second example. SP3 running continuously and without boluses provides the highest rating (5), which is even higher than when SP3 is provided in boluses (4). This might indicate that bolus stimulation is not indicated for this patient.

In a third example, notice that SP3 running continuously and without boluses rates as high (5) as when that same stimulation program is provided in boluses (with duration=30 min, and off-time=90 minutes). Given these results, it would be preferred to provide stimulation in bolus form, because such stimulation as is effective as when stimulation is provided continuously. Further, providing bolus stimulation lessens the risk of over-stimulating the patient, and saves power.

Boluses of stimulation can also be provided to a patient using other types of implantable systems, including RF systems using an External Power Supply (EPS) 604, as described earlier with respect to FIG. 6. When such a system is used, boluses are provided by simply wearing the EPS 604 at times when stimulation is desired (bolus durations), and not wearing the EPS when simulation is not desired (off-times). In this regard, scheduling of bolus therapy using an external device such as an external controller 45 or clinician programmer 50 may not involve actual control of the IPG 10. Instead, such scheduling may alert the patient as to when the EPS 604 should be worn and removed, which effectively causes the IPG 10 to provide stimulation in boluses as described herein.

The EPS 604 itself may also include the disclosed GUI or be controlled by a GUI available in a connected device (e.g., a clinician programmer or a phone app), and may be programmed with and store bolus programs, meaning that external controllers or clinician programmers are not needed. As such, an EPS 604 can, based on its programming, start or stop a bolus in accordance with a programmed schedule as discussed above, and as such can turn on or turn off stimulation regardless whether the patient is wearing or has removed the EPS. The EPS 604 can notify the patient when it has begun (or is planning to begin) a particular bolus so that the patient can wear the EPS at that time, and can notify the patient when the bolus has stopped so that the patient can remove the EPS. Still further, the patient may use the EPS 604 to self-administer boluses, and the EPS 604 may be programmed with lockout periods to prevent overuse of the bolus on demand functionality, as discussed above.

While particularly useful in providing stimulation to the spinal cord of a patient, the disclosed technique is also applicable to the stimulation of other neural tissues as well, such as the brain, peripheral nerves, peripheral ganglia, etc.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for providing stimulation to a patient using an implantable stimulator device and an external device in communication with the implantable stimulator device, comprising:

determining stimulation parameters for the patient to address a symptom of the patient;

providing a first option on a graphical user interface of the external device to schedule scheduled boluses of stimulation for the patient, wherein each scheduled bolus comprises a first duration during which stimulation is applied to the patient in accordance with the stimulation parameters, wherein the scheduled boluses are separated by off times of a second duration when no stimulation is provided to the patient;

providing a second option on the graphical user interface of the external device to receive from the patient at a first time an input to immediately provide an additional unscheduled bolus of stimulation in accordance with the stimulation parameters; and providing, using the implantable stimulator device, at least the scheduled boluses to neural tissue of the patient according to the schedule.

2. The method of claim 1, wherein the stimulation parameters provide sub-perception stimulation to address a symptom of the patient.

3. The method of claim 1, wherein the neural tissue comprises a spinal cord of the patient.

4. The method of claim 1, wherein the first duration of each of the scheduled boluses is 3 minutes or longer, and wherein the second duration of each of the off times is 30 minutes or greater.

5. The method of claim 1, wherein the stimulation provided during each scheduled bolus comprises a sequence of periodic pulses.

6. The method of claim 5, wherein the stimulation parameters comprise one or more of an amplitude of the pulses, a pulse width of the pulses, or a frequency of the pulses.

7. The method of claim 6, wherein the frequency is 10 kHz or less.

8. The method of claim 6, wherein the frequency is 1 kHz or less.

9. The method of claim 6, wherein the amplitude comprises a constant current amplitude.

10. The method of claim 1, wherein the first durations of the scheduled boluses vary.

11. The method of claim 1, wherein the second durations of the off times vary.

12. The method of claim 1, further comprising determining an activity of the patient.

13. The method of claim 12, wherein either or both of the first durations of the scheduled boluses or the second durations of the off times are adjusted in accordance with the determined activity.

14. The method of claim 12, wherein the stimulation parameters are determined in accordance with the determined activity.

15. The method of claim 12, wherein the activity of the patient is determined using an activity sensor.

16. The method of claim 15, wherein the activity sensor is within the implantable stimulator device.

17. The method of claim 1, wherein the stimulation parameters are determined at the external device, and wherein the schedule is determined at the external device.

18. The method of claim 1, further comprising immediately providing the additional unscheduled bolus to the neural tissue in addition to providing the scheduled boluses.

19. The method of claim 1, wherein the graphical user interface is programmed with a lockout period, further comprising immediately providing the additional unscheduled bolus of stimulation to the neural tissue only if a third duration between the first time and a preceding one of the scheduled boluses is equal to or longer than the lockout period.

20. The method of claim 19, further comprising rescheduling at least one of the scheduled boluses after the additional unscheduled bolus in accordance with the lockout period.

* * * * *